United States Patent
Davison et al.

(10) Patent No.: US 7,799,036 B2
(45) Date of Patent: *Sep. 21, 2010

(54) METHOD AND APPARATUS FOR SECURING VERTEBRAE

(75) Inventors: Thomas W. Davison, North Attleboro, MA (US); Timothy E. Taylor, Hoover, AL (US); Adam Sher, North Attleboro, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 1603 days.

This patent is subject to a terminal disclaimer.

(21) Appl. No.: 10/514,797

(22) PCT Filed: Jul. 31, 2001

(86) PCT No.: PCT/US01/23999

§ 371 (c)(1),
(2), (4) Date: Nov. 18, 2004

(87) PCT Pub. No.: WO02/09801

PCT Pub. Date: Feb. 7, 2002

(65) Prior Publication Data

US 2006/0089662 A1      Apr. 27, 2006

(51) Int. Cl.
*A61B 17/60* (2006.01)
*A61F 2/00* (2006.01)
(52) U.S. Cl. .................................................. 606/99
(58) Field of Classification Search ............... 606/53, 606/60, 86 R, 99, 246, 250
See application file for complete search history.

(56) References Cited

U.S. PATENT DOCUMENTS

| 1,170,324 | A | 2/1916 | Pomerene |
| 2,605,582 | A | 8/1952 | Allen |
| 3,044,461 | A | 7/1962 | Murdock |
| 3,503,398 | A | 3/1970 | Fogarty et al. |
| 3,789,852 | A | 2/1974 | Kim et al. |
| 3,841,317 | A | 10/1974 | Awais |
| 4,449,532 | A | 5/1984 | Storz |

(Continued)

FOREIGN PATENT DOCUMENTS

AU     A-13672/95     9/1995

(Continued)

OTHER PUBLICATIONS

U.S. Appl. No. 11/417,659, filed May 3, 2006, Davison et al.

(Continued)

*Primary Examiner*—Anu Ramana
(74) *Attorney, Agent, or Firm*—Crompton, Seager & Tufte, LLC.

(57) ABSTRACT

A method of fixing vertebrae of a patient together at a surgical site includes the following steps: inserting a first cannula (10) into the body (130) of the patient; moving a first fastener (624) through the cannula (10) and securing the first fastener (624) through the cannula (10) and securing the first fastener (624) to a first vertebrae (601 or 1601); moving a second fastener (624) through the cannula (10) and securing the second fastener (624) to a second vertebrae (602 or 1602); moving a first fixation element (650) through the cannula (10); and fixing the first fixation element (650) to the first and second fasteners (624).

43 Claims, 20 Drawing Sheets

U.S. PATENT DOCUMENTS

| | | |
|---|---|---|
| 4,451,256 A | 5/1984 | Weikl et al. |
| 4,545,374 A | 10/1985 | Jacobson |
| 4,573,448 A | 3/1986 | Kambin |
| 4,601,713 A | 7/1986 | Fuqua |
| 4,611,594 A | 9/1986 | Grayhack et al. |
| 4,617,929 A | 10/1986 | Gill |
| 4,716,901 A | 1/1988 | Jackson et al. |
| 4,817,587 A | 4/1989 | Janese |
| 4,819,620 A | 4/1989 | Okutsu |
| 4,863,133 A | 9/1989 | Bonnell |
| 4,899,729 A | 2/1990 | Gill et al. |
| 4,921,478 A | 5/1990 | Solano et al. |
| 4,984,564 A | 1/1991 | Yuen |
| 5,025,778 A | 6/1991 | Silverstein et al. |
| 5,131,382 A | 7/1992 | Meyer |
| 5,139,499 A | 8/1992 | Small et al. |
| 5,139,511 A | 8/1992 | Gill et al. |
| 5,163,949 A | 11/1992 | Bonutti |
| 5,171,279 A | 12/1992 | Mathews |
| 5,190,561 A | 3/1993 | Graber |
| 5,195,541 A | 3/1993 | Obenchain |
| 5,196,023 A | 3/1993 | Martin |
| 5,197,971 A | 3/1993 | Bonutti |
| 5,224,680 A | 7/1993 | Greenstein et al. |
| 5,232,443 A | 8/1993 | Leach |
| 5,279,564 A | 1/1994 | Taylor |
| 5,287,845 A | 2/1994 | Faul et al. |
| 5,295,994 A | 3/1994 | Bonutti |
| 5,312,417 A | 5/1994 | Wilk |
| 5,313,962 A | 5/1994 | Obenchain |
| 5,345,927 A | 9/1994 | Bonutti |
| 5,346,504 A | 9/1994 | Ortiz et al. |
| 5,354,302 A | 10/1994 | Ko |
| 5,370,647 A | 12/1994 | Graber et al. |
| 5,370,659 A | 12/1994 | Sakashita |
| 5,395,317 A | 3/1995 | Kambin |
| 5,417,203 A | 5/1995 | Tovey et al. |
| 5,439,464 A | 8/1995 | Shapiro |
| 5,443,479 A | 8/1995 | Bressi, Jr. |
| 5,454,365 A | 10/1995 | Bonutti |
| 5,472,426 A | 12/1995 | Bonati et al. |
| 5,484,437 A | 1/1996 | Michelson |
| 5,489,307 A | 2/1996 | Kuslich et al. |
| 5,490,819 A | 2/1996 | Nicholas et al. |
| 5,503,617 A | 4/1996 | Jako |
| 5,520,607 A | 5/1996 | Frassica et al. |
| 5,529,571 A | 6/1996 | Daniel |
| 5,556,376 A | 9/1996 | Yoon |
| 5,571,072 A | 11/1996 | Kronner |
| 5,575,754 A | 11/1996 | Konomura |
| 5,601,590 A | 2/1997 | Bonutti et al. |
| 5,601,690 A | 2/1997 | Gauld et al. |
| 5,643,282 A | 7/1997 | Kieturakis |
| 5,649,902 A | 7/1997 | Yoon |
| 5,667,520 A | 9/1997 | Bonutti |
| 5,690,606 A | 11/1997 | Slotman |
| 5,707,359 A | 1/1998 | Bufalini |
| 5,762,629 A | 6/1998 | Kambin |
| 5,782,919 A | 7/1998 | Zdeblick et al. |
| 5,792,044 A | 8/1998 | Foley et al. |
| 5,795,289 A | 8/1998 | Wyttenbach |
| 5,813,978 A | 9/1998 | Jako |
| 5,817,062 A | 10/1998 | Flom et al. |
| 5,827,319 A | 10/1998 | Carlson et al. |
| 5,851,214 A | 12/1998 | Larsen et al. |
| 5,865,802 A | 2/1999 | Yoon et al. |
| 5,902,231 A | 5/1999 | Foley et al. |
| 5,954,635 A | 9/1999 | Foley et al. |
| 5,961,499 A | 10/1999 | Bonutti et al. |
| 5,964,761 A * | 10/1999 | Kambin ..................... 606/304 |
| 5,976,161 A | 11/1999 | Kirsch et al. |
| 5,997,508 A | 12/1999 | Lunn et al. |
| 6,036,638 A | 3/2000 | Nwawka |
| 6,120,437 A | 9/2000 | Yoon et al. |
| 6,126,671 A | 10/2000 | Richards et al. |
| 6,152,871 A | 11/2000 | Foley et al. |
| 6,162,236 A | 12/2000 | Osada |
| 6,171,299 B1 | 1/2001 | Bonutti |
| 6,175,758 B1 | 1/2001 | Kambin |
| 6,187,000 B1 | 2/2001 | Davison et al. |
| 6,254,628 B1 | 7/2001 | Wallace et al. |
| 6,306,170 B2 | 10/2001 | Ray |
| 6,312,443 B1 | 11/2001 | Stone |
| 6,338,730 B1 | 1/2002 | Bonutti et al. |
| 6,358,266 B1 | 3/2002 | Bonutti |
| 6,361,488 B1 | 3/2002 | Davison et al. |
| 6,371,968 B1 | 4/2002 | Kogasaka |
| 6,383,195 B1 | 5/2002 | Richard |
| 6,432,048 B1 | 8/2002 | Francois |
| 6,494,893 B2 | 12/2002 | Dubrul et al. |
| 6,497,654 B1 | 12/2002 | Leonard et al. |
| 6,524,320 B2 | 2/2003 | DiPoto |
| 6,530,880 B2 | 3/2003 | Pagliuca |
| 6,530,926 B1 | 3/2003 | Davison |
| 6,564,078 B1 | 5/2003 | Marino et al. |
| 6,589,225 B2 | 7/2003 | Orth et al. |
| 6,620,129 B2 | 9/2003 | Stecker et al. |
| 6,648,888 B1 | 11/2003 | Shluzas |
| 6,652,553 B2 | 11/2003 | Davison et al. |
| 6,800,084 B2 | 10/2004 | Davison et al. |
| 6,811,558 B2 | 11/2004 | Davison et al. |
| 6,837,891 B2 | 1/2005 | Davison et al. |
| 7,001,397 B2 | 2/2006 | Davison et al. |
| 7,033,369 B2 | 4/2006 | Davison et al. |
| 7,056,321 B2 | 6/2006 | Pagliuca et al. |
| 7,108,705 B2 | 9/2006 | Davison et al. |
| 7,144,393 B2 | 12/2006 | DiPoto et al. |
| 2001/0011170 A1 | 8/2001 | Davison et al. |
| 2001/0049498 A1 | 12/2001 | Davison et al. |
| 2002/0002360 A1 | 1/2002 | Orth et al. |
| 2003/0009130 A1 | 1/2003 | Stecker et al. |
| 2003/0014068 A1 | 1/2003 | Bonutti et al. |
| 2003/0040656 A1 | 2/2003 | Pagliuca et al. |
| 2003/0073998 A1 | 4/2003 | Pagliuca et al. |
| 2003/0083688 A1 | 5/2003 | Simonson |
| 2003/0083689 A1 | 5/2003 | Simonson |
| 2003/0139648 A1 | 7/2003 | Foley et al. |
| 2003/0153911 A1 | 8/2003 | Shluzas |
| 2003/0153927 A1 | 8/2003 | DiPoto et al. |
| 2003/0167058 A1 | 9/2003 | Shluzas |
| 2003/0191371 A1 | 10/2003 | Smith et al. |
| 2003/0195405 A1 | 10/2003 | Marino et al. |
| 2003/0195493 A1 | 10/2003 | Davison et al. |
| 2003/0195549 A1 | 10/2003 | Davison et al. |
| 2003/0195550 A1 | 10/2003 | Davison et al. |
| 2003/0195551 A1 | 10/2003 | Davison et al. |
| 2003/0199871 A1 | 10/2003 | Foley et al. |
| 2003/0199885 A1 | 10/2003 | Davison et al. |
| 2003/0236529 A1 | 12/2003 | Shluzas et al. |
| 2004/0059339 A1 | 3/2004 | Roehm, III et al. |
| 2004/0078051 A1 | 4/2004 | Davison et al. |
| 2004/0093002 A1 | 5/2004 | Davison et al. |
| 2004/0097907 A1 | 5/2004 | DiPoto |
| 2004/0098012 A1 | 5/2004 | Davison et al. |
| 2004/0116954 A1 | 6/2004 | Pagliuca et al. |
| 2004/0133201 A1 | 7/2004 | Shluzas et al. |
| 2004/0236317 A1 | 11/2004 | Davison |
| 2005/0021030 A1 | 1/2005 | Pagliuca et al. |
| 2005/0033297 A1* | 2/2005 | Davison ..................... 606/61 |
| 2005/0043754 A1* | 2/2005 | Davison et al. ............. 606/198 |
| 2005/0075540 A1 | 4/2005 | Shluzas et al. |
| 2005/0113833 A1 | 5/2005 | Davison |
| 2006/0264999 A1* | 11/2006 | Davison et al. ............. 606/198 |

| | | | |
|---|---|---|---|
| 2006/0276821 A1* | 12/2006 | Davison et al. | 606/198 |
| 2006/0276822 A1 | 12/2006 | Davison et al. | |

FOREIGN PATENT DOCUMENTS

| | | | |
|---|---|---|---|
| EP | 0 528 562 A2 | 2/1993 | |
| EP | 0 807 415 A2 | 11/1997 | |
| EP | 0 807 415 A3 | 8/1998 | |
| EP | 0 980 677 A1 | 2/2000 | |
| EP | 1 305 077 A1 | 5/2003 | |
| FR | 2 701 379 A1 | 8/1994 | |
| JP | 2000-83960 A2 | 3/2000 | |
| JP | 2001-149376 A2 | 6/2001 | |
| WO | WO 92/21292 A2 | 12/1992 | |
| WO | WO 93/14801 A1 | 8/1993 | |
| WO | WO 94/03114 A1 | 2/1994 | |
| WO | WO 95/10218 A1 | 4/1995 | |
| WO | WO 95/22285 A1 | 8/1995 | |
| WO | WO 95/32663 A1 | 12/1995 | |
| WO | WO 01/54560 A2 | 8/2001 | |
| WO | WO 01/54560 A3 | 8/2001 | |
| WO | WO 02/09801 A1 | 2/2002 | |
| WO | WO 02/078767 A2 | 10/2002 | |
| WO | WO 03/007783 A2 | 1/2003 | |

OTHER PUBLICATIONS

"Arthroscopic Lumbar Intervertebral Fusion" by Kambin, Adult Spine: Principles and Practice, pp. 2037-2046 (1997).

"Arthroscopic Techniques for Spinal Surgery" by Kambin, Operative Arthroscopy, Second Edition, pp. 1215-1225 (1996).

"Diagnostic and Therapeutic Spinal Arthroscopy" by Kambin, Neurosurgery Clinics of North America, vol. 7, No. 1, pp. 65-76 (Jan. 1996).

"The Role of Minimally Invasive Surgery in Spinal Disorders" by Kambin, Advances in Operative Orthopedics, vol. 3, pp. 147-171 (1995).

"Arthroscopic Microdiskectomy" by Kambin, Mount Sinai J. of Medicine, pp. 159-164 (Mar. 1991).

Ditsworth, David A., M.D., *Surg Neurol*, 49; 588-598, 1998 "Endoscopic Transforaminal Lumbar Discectomy and Reconfiguration: A Postero-lateral Approach into the Spinal Canal".

Endius Marketing Bulletin, 2002, Atavi Atraumatic Spine Fusion System, "How do I decompress using Atavi System?".

Endius Marketing Bulletin, 2002, Atavi Atraumatic Spine Fusion System "Minimally Invasive Update on Danek".

Foley, Kevin T., M.D., Gupta, Sanjay K., M.D., Justis, Jeff R., B.S., Sherman, Michael C., M.S., *Neurosurg Focus*, 10: 1-8, 2001 "Percutaneous pedicle screw fixation of the lumbar spine".

Guiot, Bernard H., M.D., Khoo, Larry T., M.D., Fessler, Richard G., M.D., Ph.D., *SPINE*, 27, 4: 432-438, 2002 "A Minimally Invasive Technique for Decompression of the Lumbar Spine".

Kambin, Parviz, Publisher Unknown, Chapter 77:1055-1066, Date Unknown "Arthroscopic Lumbar Interbody Fusion".

Kambin, Parviz, Publisher Unknown, Chapter 9:117-121, Date Unknown "Posterolateral Percutaneous Lumbar Interbody Fusion".

Medtronic Sofamor Danek, *METRx MicroEndoscopic Discectomy*, 1999 "An Evolution in Minimally Invasive Spine Surgery".

Medtronic Sofamor Danek, *METRx MicroDiscectomy System*, 2000 "The Next Step in Minimally Invasive Discectomy Utilizing The Operating Microscope".

Medtronic Sofmor Danek, *METRx Microdiscectomy Surgical Technique*, 2001 as described by: Donald L. Hilton, Jr., M.D., F.A.C.S. and Sylvain Palmer, M.D., F.A.C.S.

Medtronic Sofamor Danek, *Orthopedics Today*, 1-20, 2002 "Minimal Access Spinal Technologies".

MicroEndoscopic Discectomy System by Sofamor Danek USA, dated 1996 (pp. 1-33) A manual entitled "MED™".

Stauber, Martin H., M.D., Bassett, George S., M.D., *SPINE*, 19, 1: 57-61, 1994 Pedicle Screw Placement With Intraosseous Endoscopy.

"Arthroscopic Fusion of the Lumbosacral Spine", Parviz Kambin, MD and Jonathan L. Schaffer, MD, Lumbosacral and Spinopelvic Fixation, 44:565-577, 1996.

Caspar, Wolfhard, M.D., et al."The Caspar Microsurgical Discectomy and Comparison with a Conventional Standard Lumbar Disc Procedure," Neurosurgery, Jan. 1991, pp. 78-87, vol. 28, No. 1, Williams & Wilkins, Baltimore, MD.

Amendment filed on Aug. 3, 2005 in U.S. Appl. No. 10/440,002.

Amendment filed on Oct. 5, 2004 in U.S. Appl. No. 10/439,979.

* cited by examiner

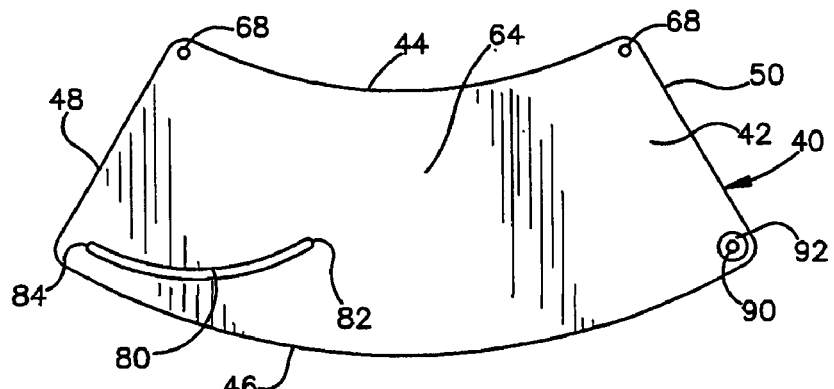
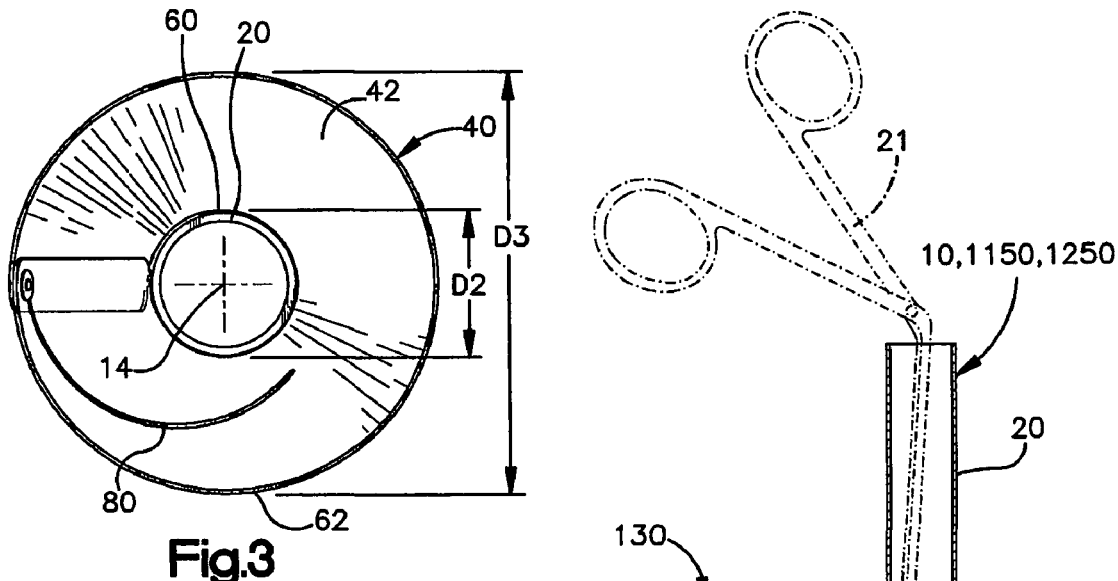
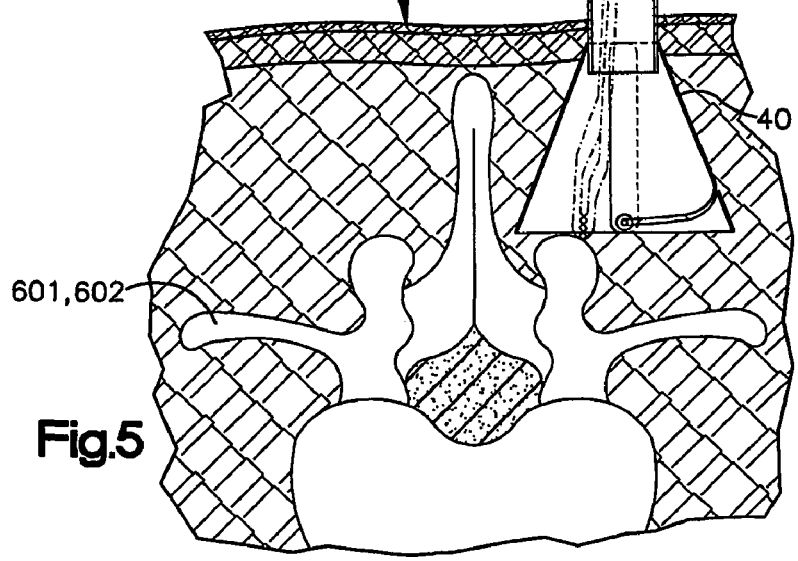

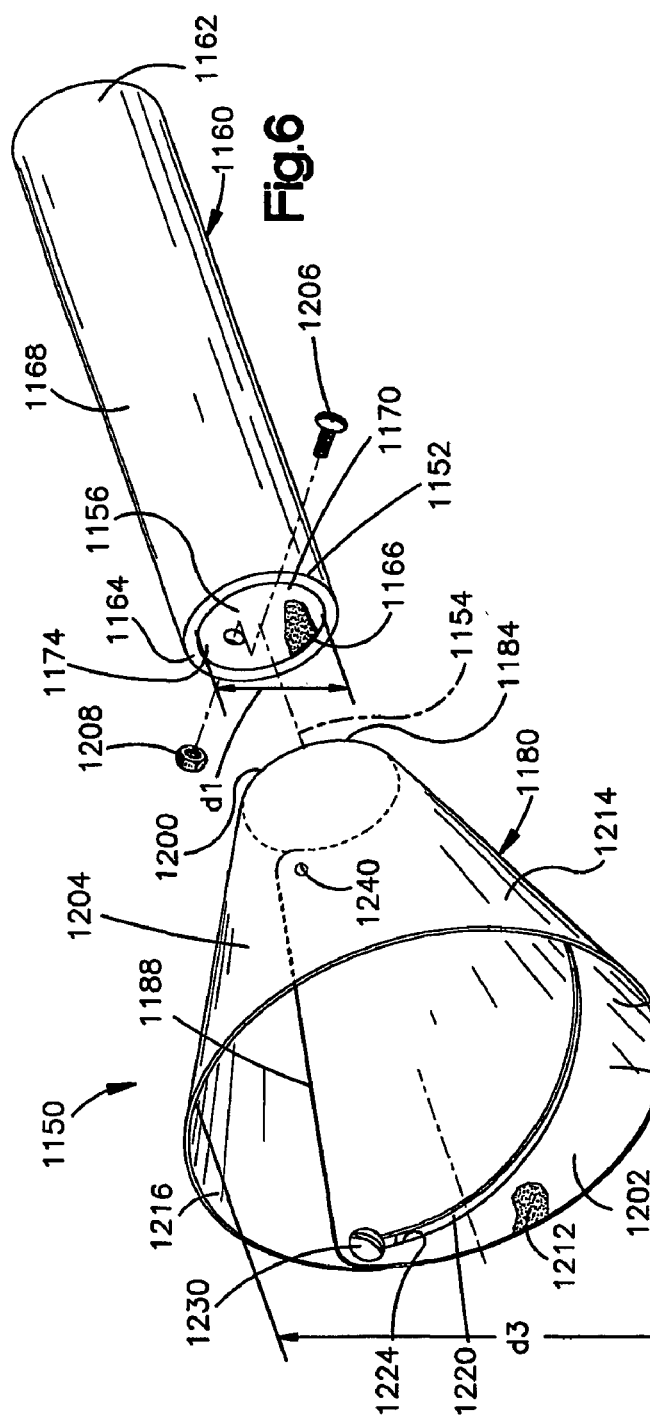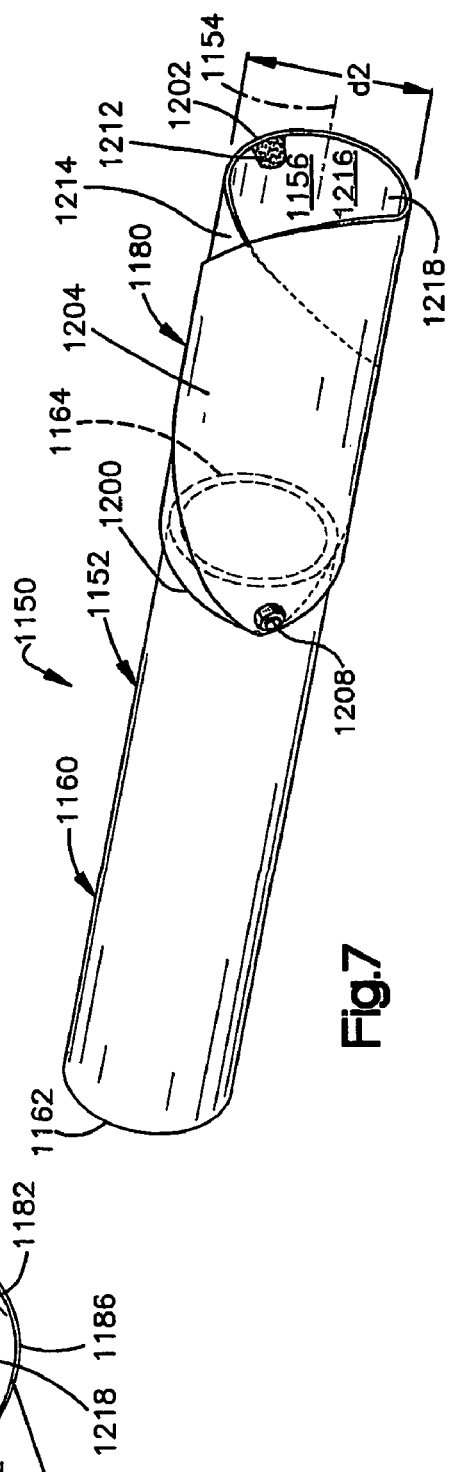

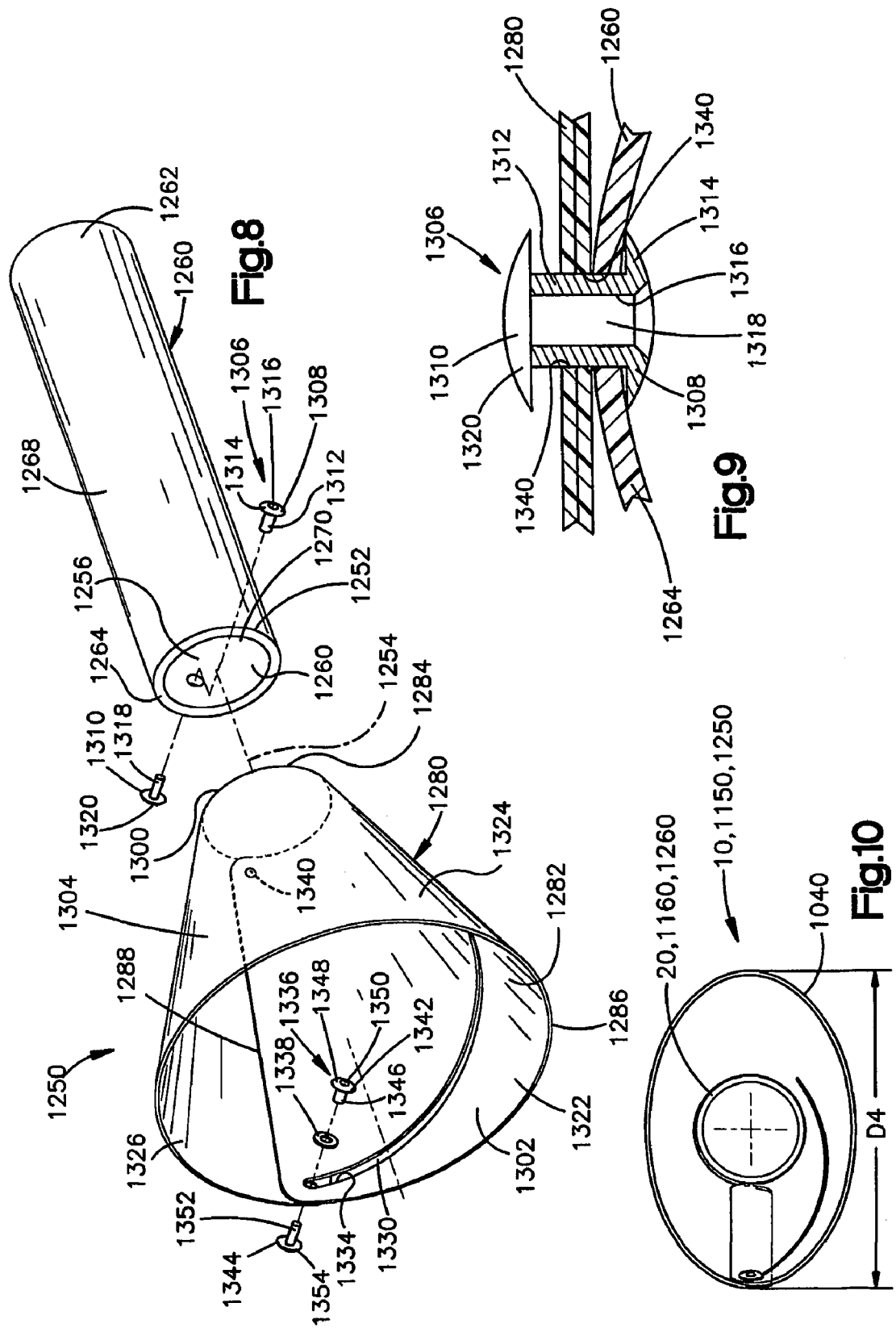

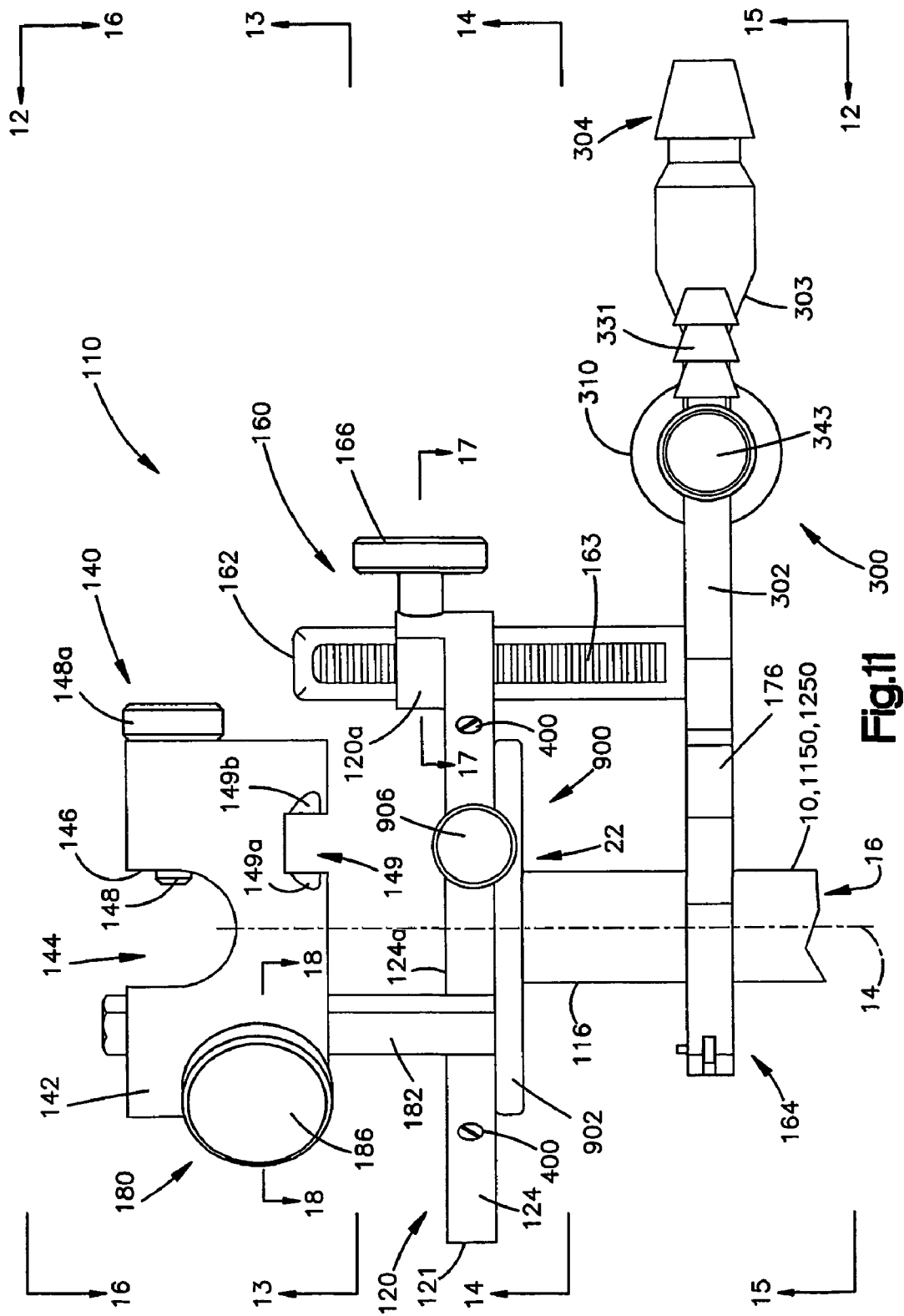

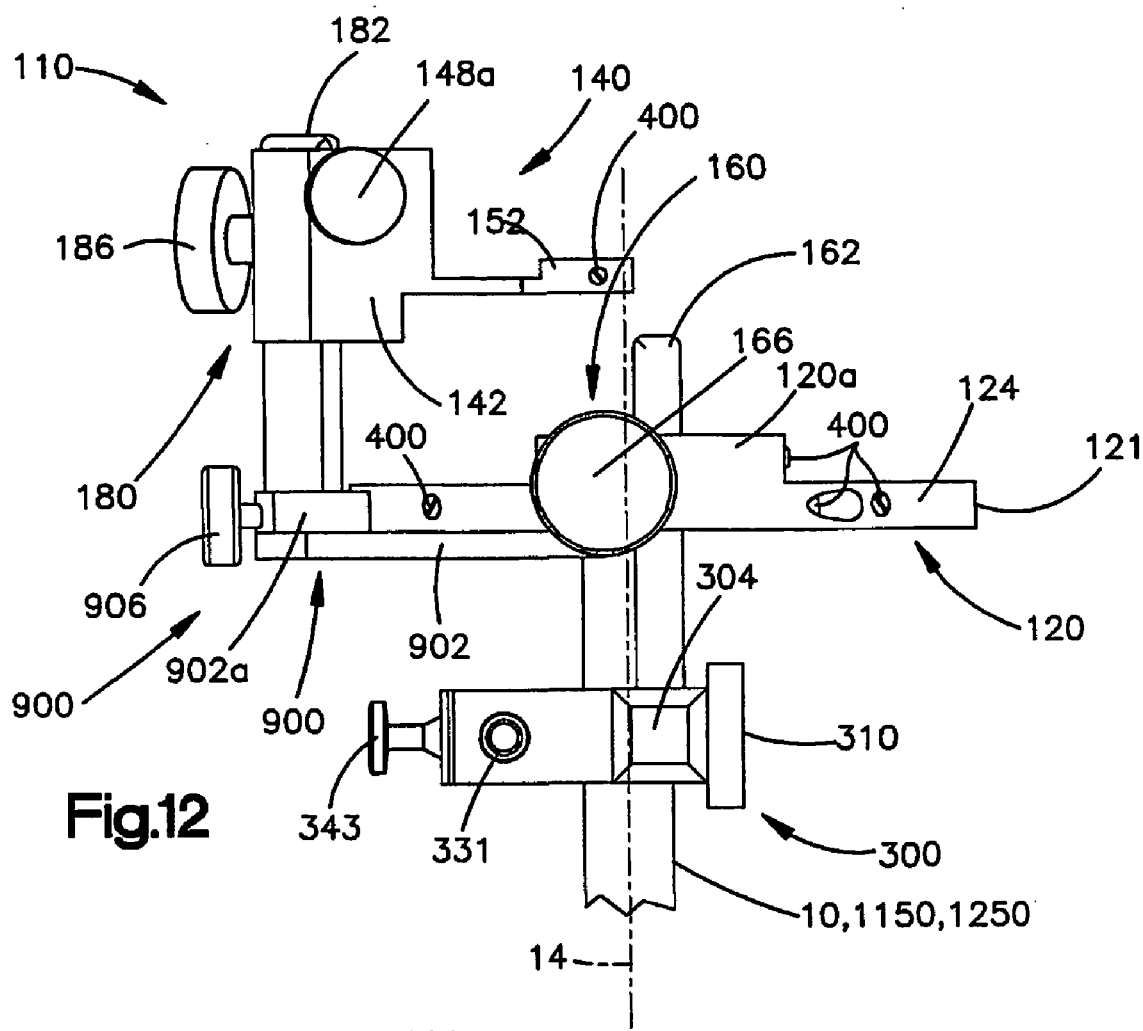
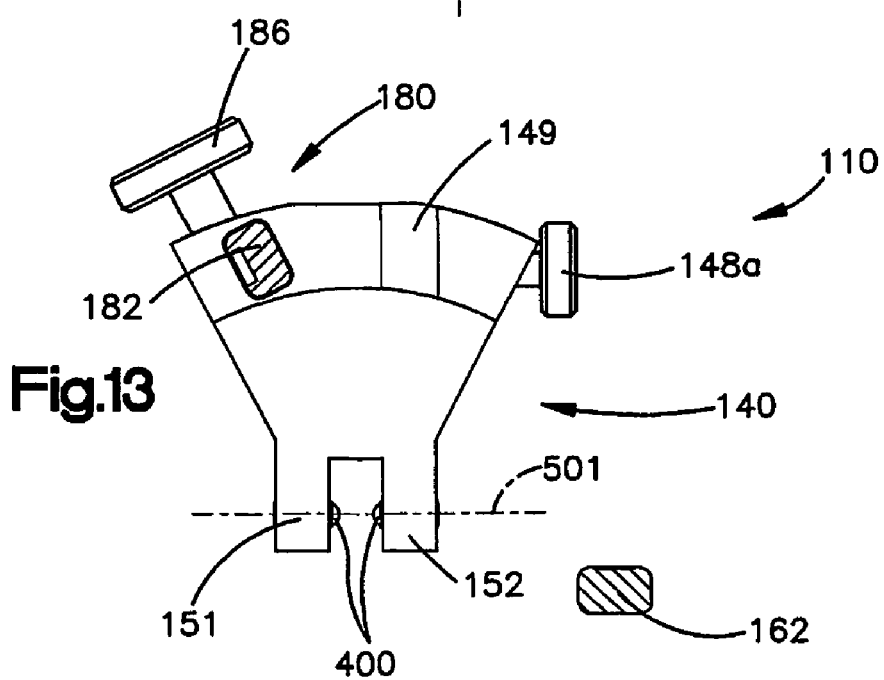

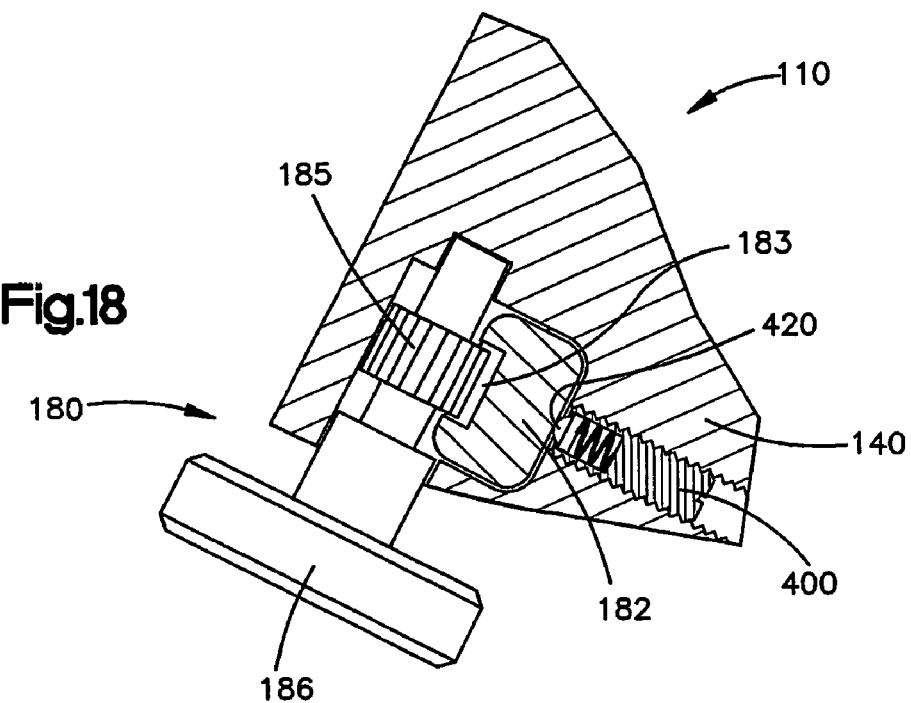
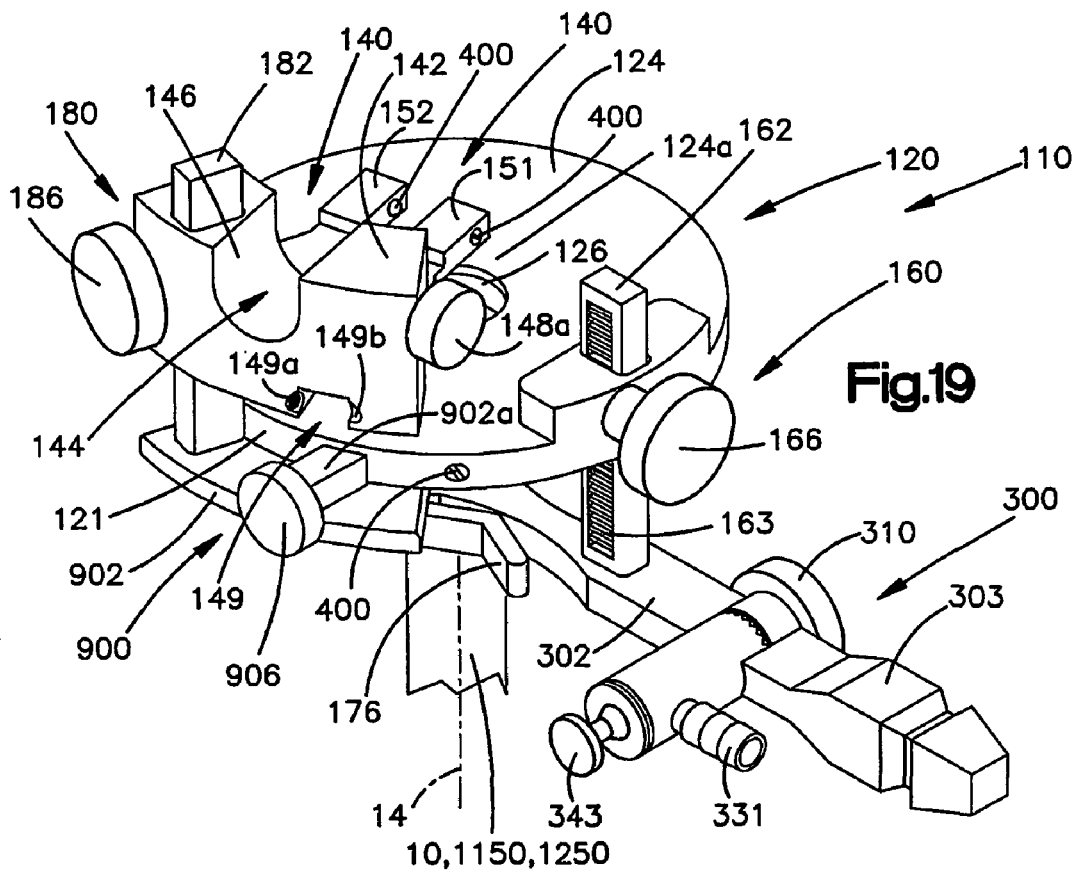

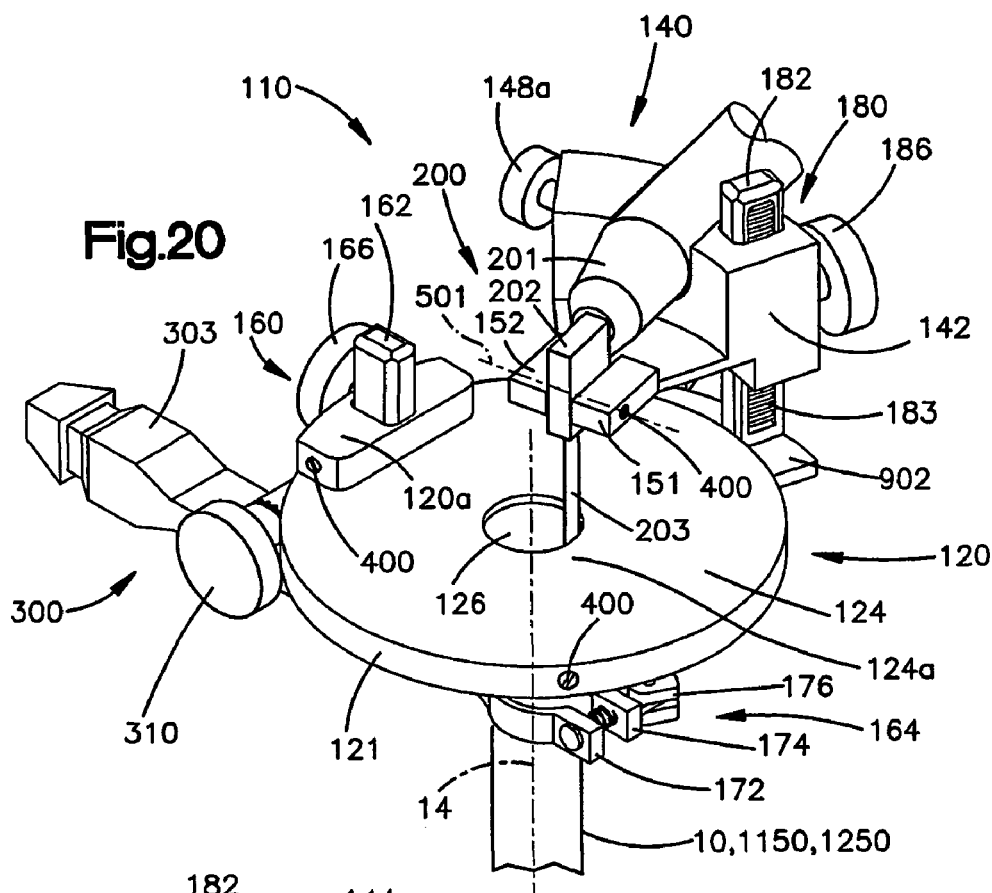
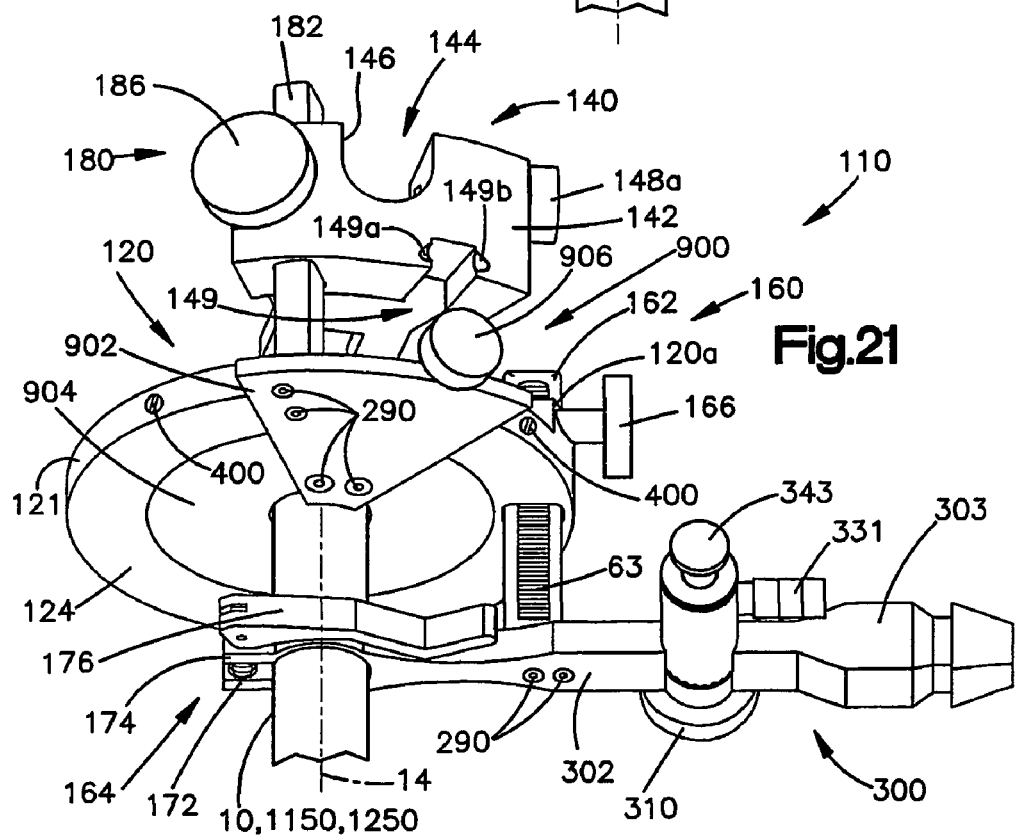

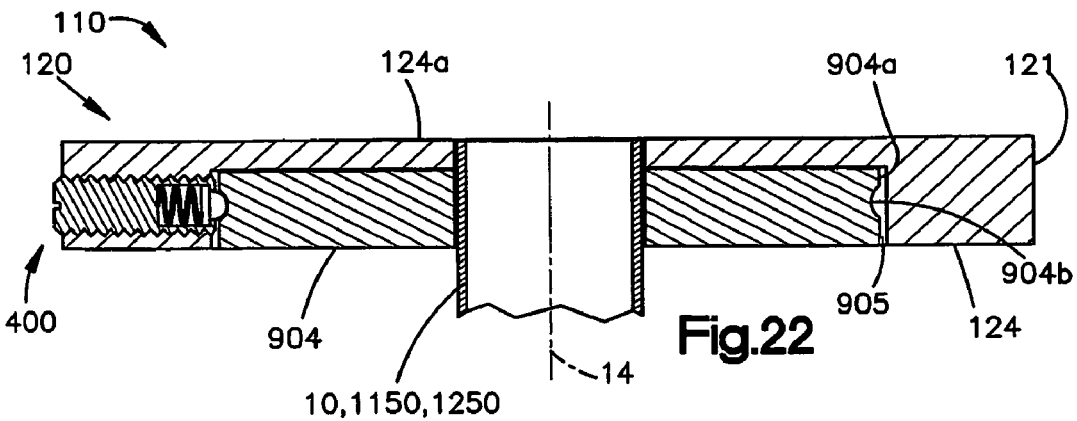
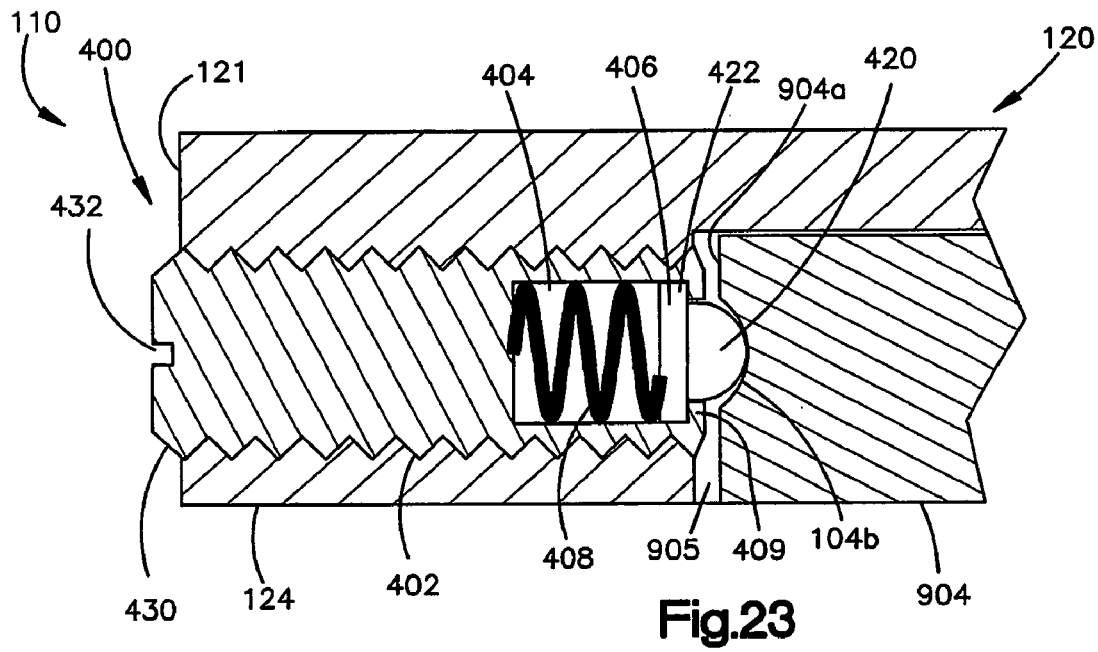
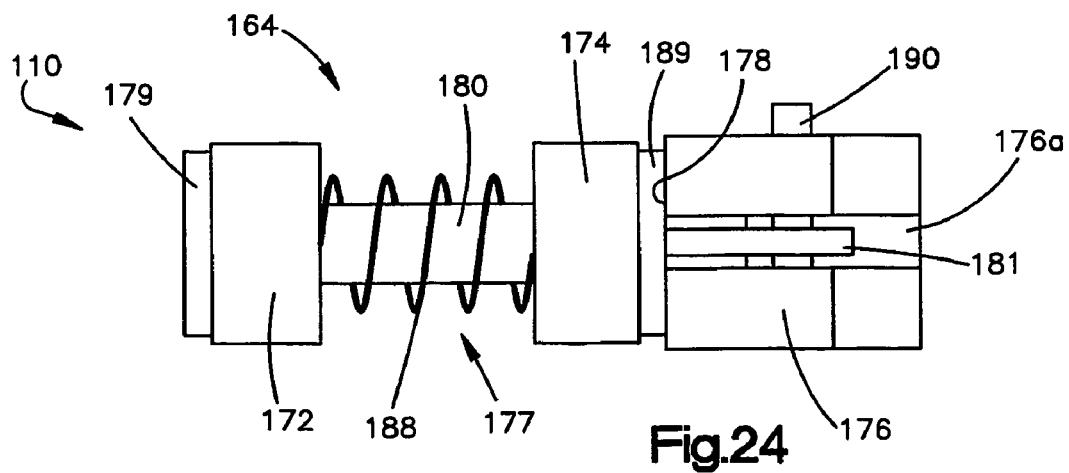

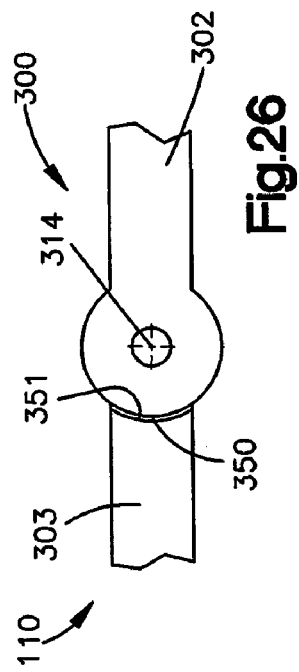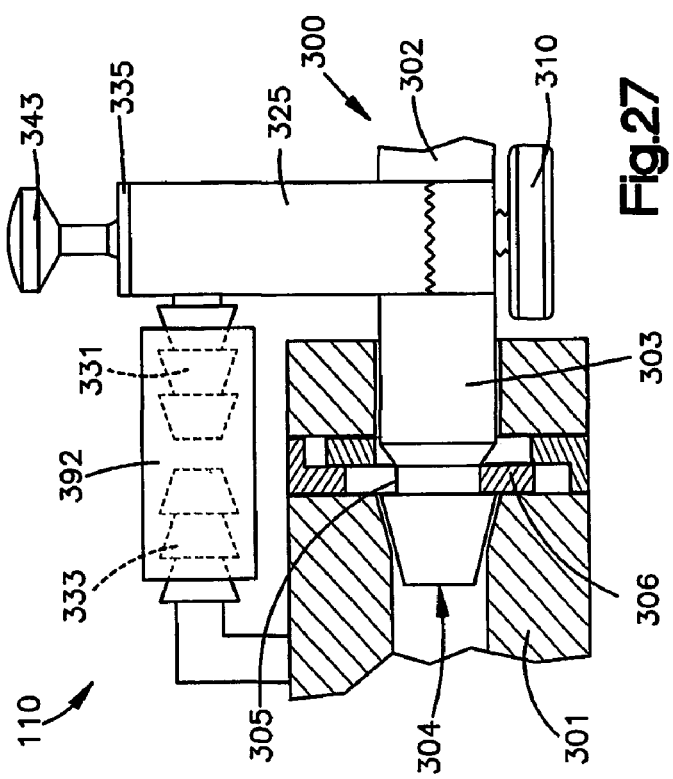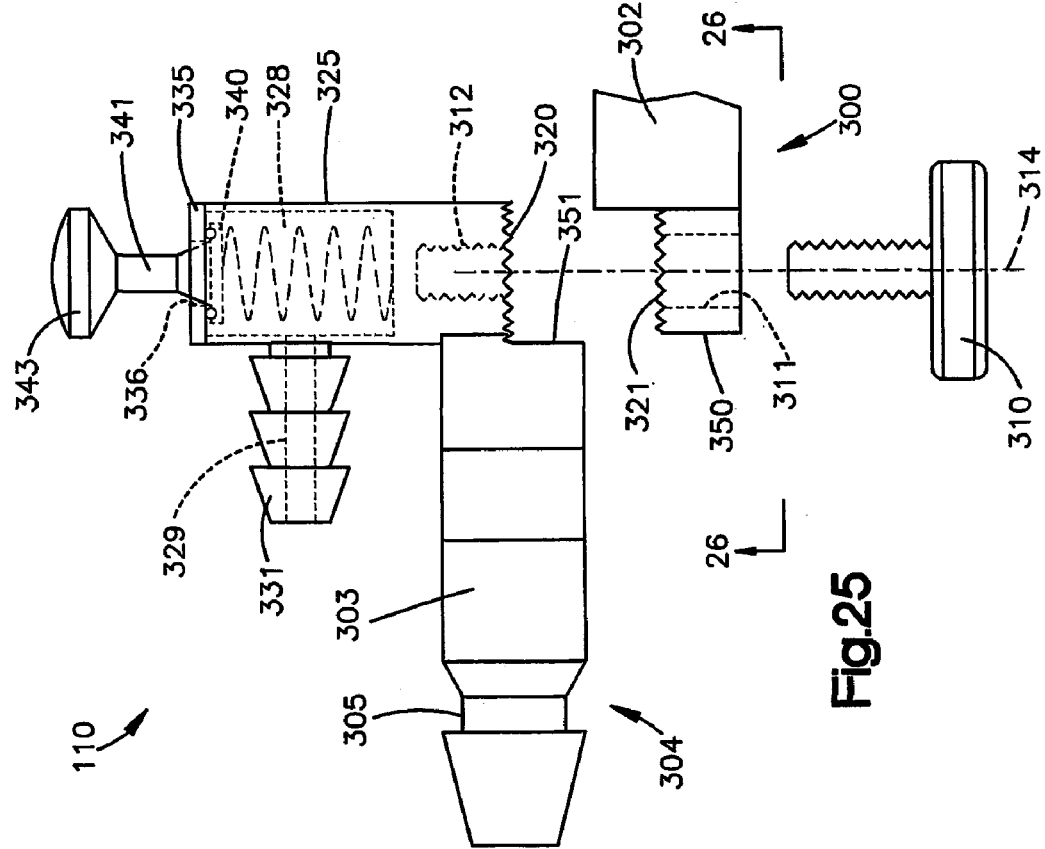

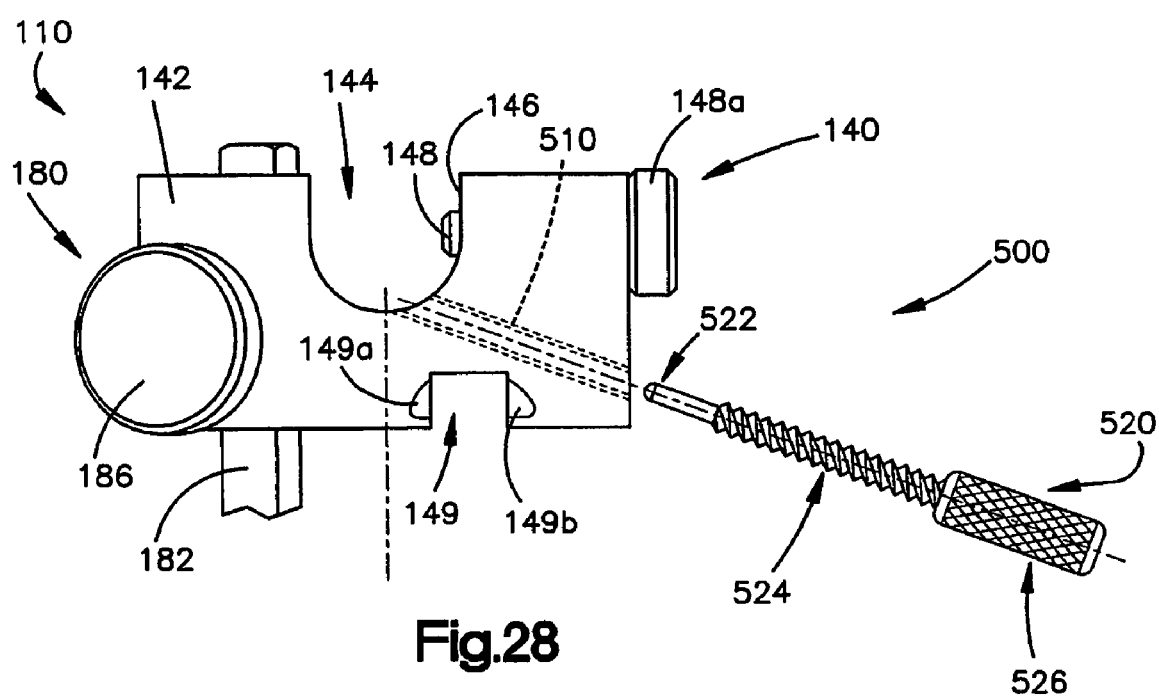

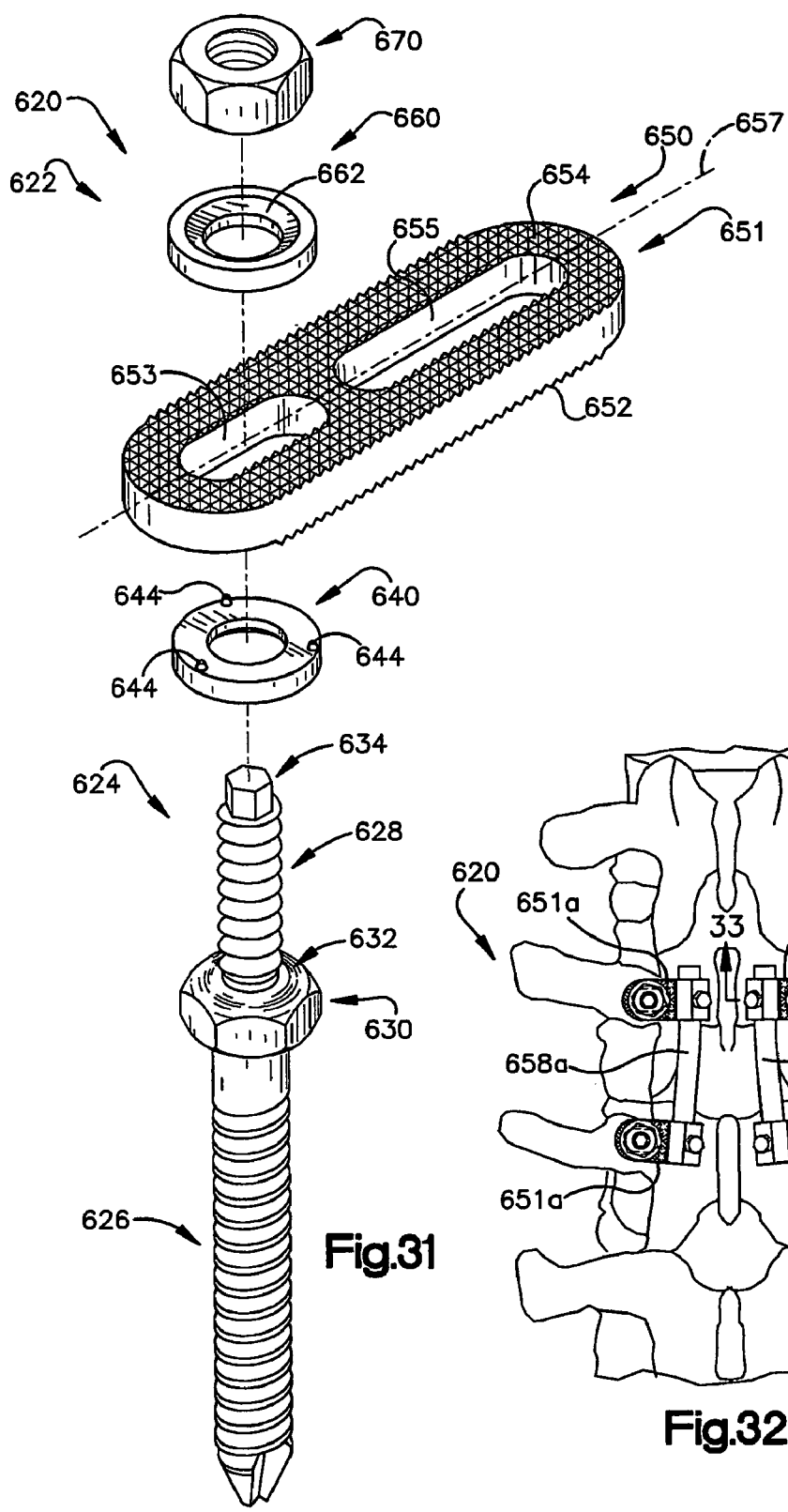
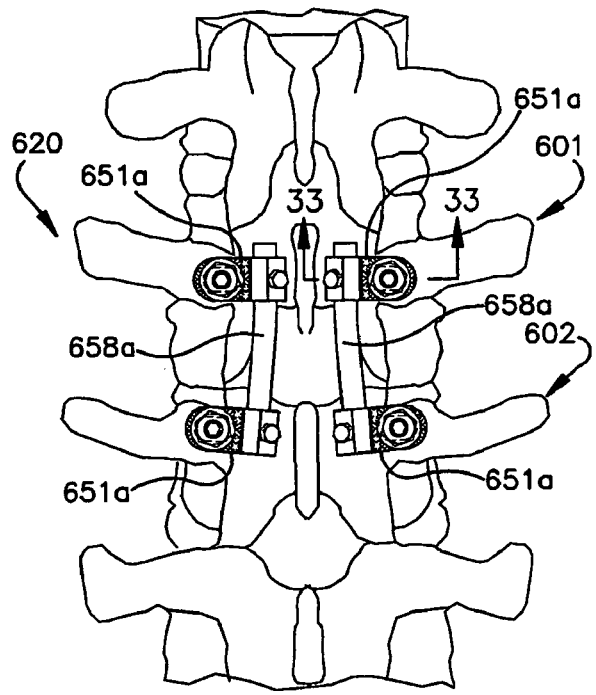
Fig.31
Fig.32

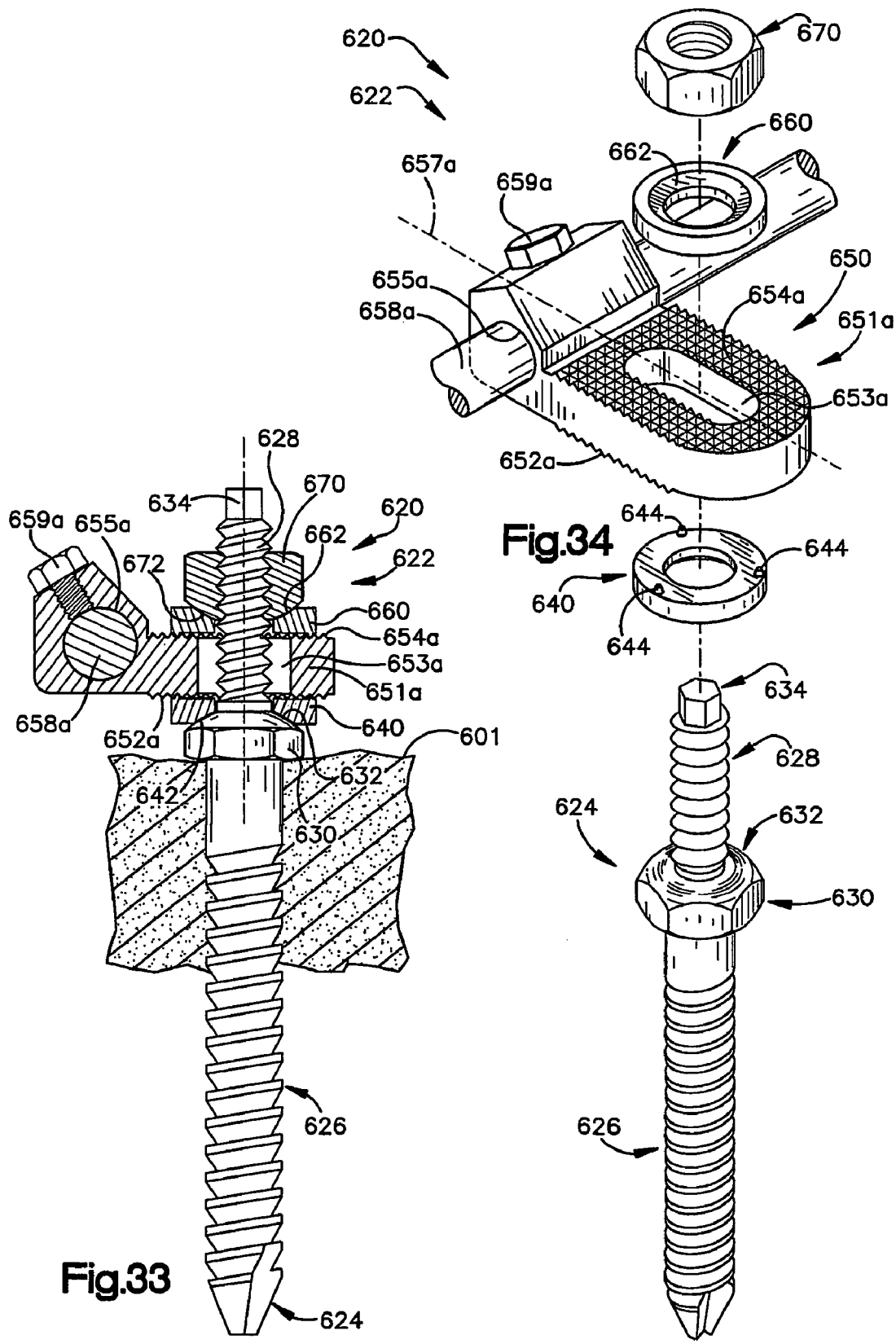

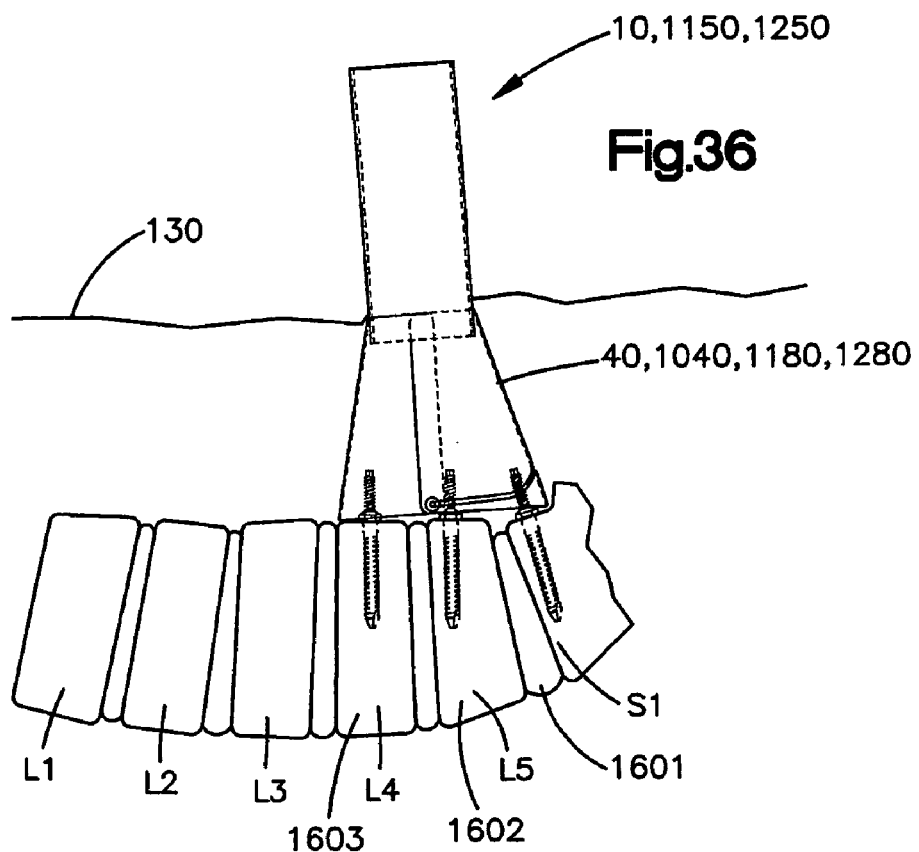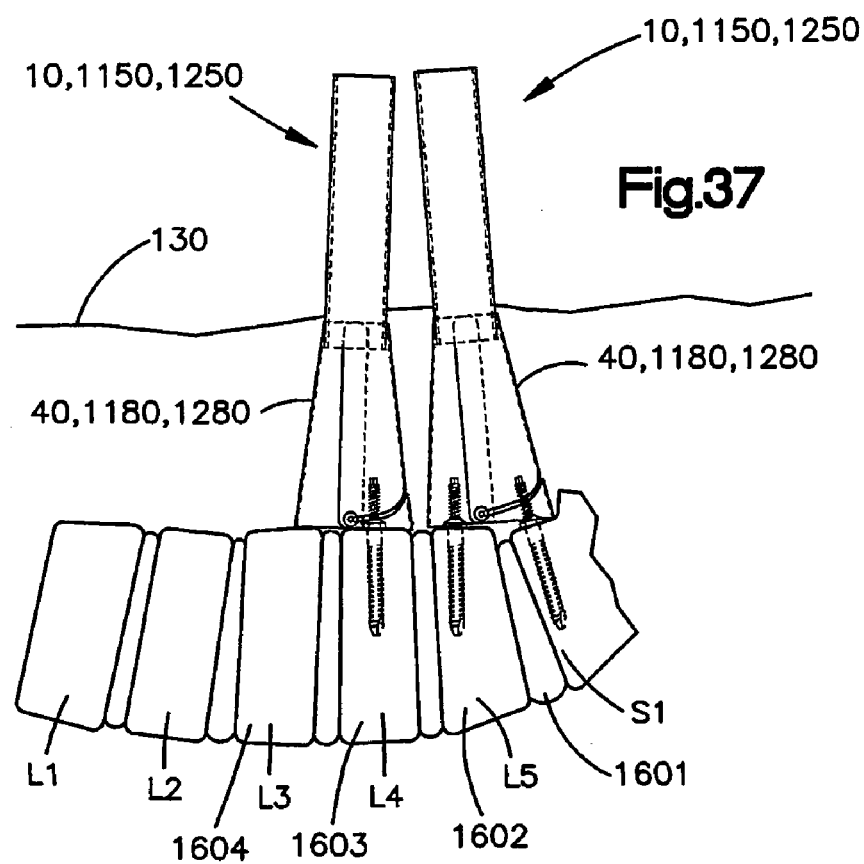

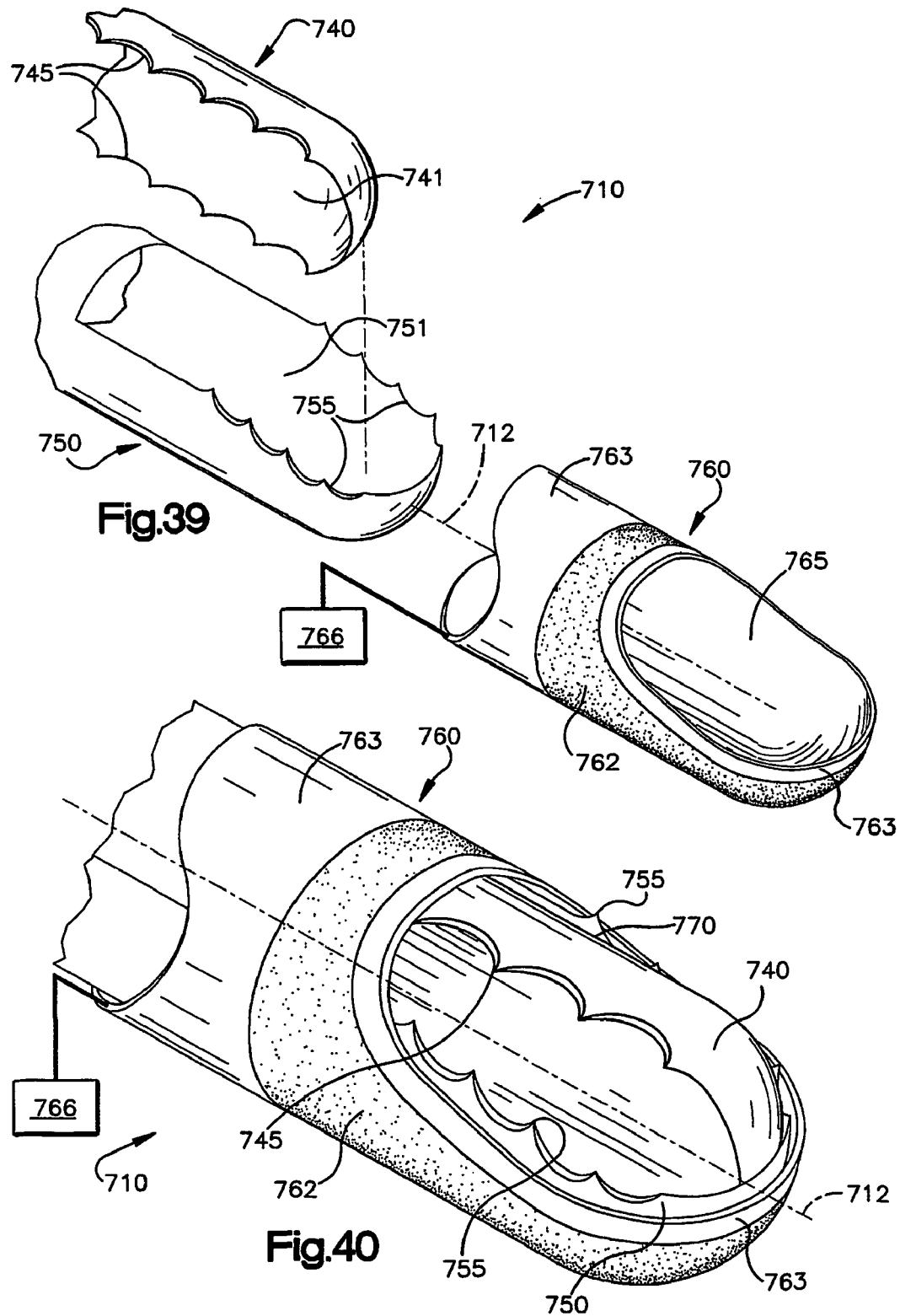

US 7,799,036 B2

METHOD AND APPARATUS FOR SECURING VERTEBRAE

TECHNICAL FIELD

The present invention relates to a method and apparatus for performing a surgical procedure on a body of a patient, and more particularly, to a method and apparatus for fixing vertebrae of a patient together at a surgical site.

BACKGROUND OF THE INVENTION

Percutaneous surgery is a procedure in which surgical instruments and an endoscope are inserted through a cannula into the body of a patient. A viewing element, typically a small video camera, is part of the endoscope and is connected to a monitor so that the surgeon may view the surgical site.

The cannula is a hollow tube that is inserted through an incision into the body of a patient so that a distal end of the cannula lies adjacent the surgical site. The cannula holds the incision open and serves as a conduit extending between the exterior of the body of the patient and the local area inside the body where the surgery will be performed. The instruments, usually one at a time, and the endoscope are inserted through the cannula. The cannula also allows the instruments and the endoscope to be removed from the body and/or adjusted in the body during the surgery without trauma to the body.

A conventional apparatus for supporting the cannula and the endoscope allows a surgeon to manipulate the surgical instruments without also moving the endoscope. Also, a known support apparatus allows adjustment of the endoscope relative to the cannula for viewing different areas of the surgical site in the body.

While the above described method and apparatus enables many types of surgeries at small surgical sites, the fixing of vertebrae together has heretofore been conducted by a much more invasive open surgical method.

SUMMARY OF THE INVENTION

In accordance with one feature of the present invention, a method of fixing vertebrae of a patient together at a surgical site includes the following steps: inserting a first cannula into the body of the patient; moving a first fastener through the cannula; securing the first fastener to a first vertebrae; moving a second fastener through the cannula; securing the second fastener to a second vertebrae; moving a first fixation element through the cannula; and fixing the first fixation element to the first and second fasteners.

In accordance with another feature of the present invention, a method of performing a surgical procedure on a body includes the following steps: providing a cannula having a tubular structure with first and second tubular portions defining first and second passages for receiving surgical instruments, the second passage being a continuation of the first passage; inserting the cannula through an incision in the body, the inserting step including inserting the second tubular portion inside the body and inserting the first tubular portion into the incision so that the first tubular portion extends from an exterior of the body to inside the body; expanding the second tubular portion of the cannula to increase the cross-sectional area of the second passage in the second tubular portion while the second tubular portion is inside the body; and maintaining the cross-sectional area of the first passage in the first tubular portion while expanding the second tubular portion of the cannula.

In accordance with still another feature of the present invention, a cannula is used for receiving surgical instruments. The cannula includes a first tubular portion defining a first passage for receiving the surgical instruments and a second tubular portion. The first tubular portion has a first thickness measured in a direction perpendicular to inner and outer surfaces of the first tubular portion. The second tubular portion is attached to the first tubular portion and defines a second passage for receiving the surgical instruments. The second passage is a continuation of the first passage. The second tubular portion has a thickness measured perpendicular to inner and outer surfaces of the second tubular portion. The first thickness is different than the second thickness.

In accordance with yet another feature of the present invention, a cannula is used for receiving surgical instruments. The cannula includes a first tubular portion and a second tubular portion. The first tubular portion has a first outer surface for engaging the body and a first inner surface defining a first passage for receiving the surgical instruments. The first tubular portion has a proximal end and an opposite distal end. The second tubular portion is attached to the distal end of the first tubular portion. The second tubular portion has a second outer surface for engaging the body and a second inner surface defining a second passage for receiving the surgical instruments. The second passage is a continuation of said first passage. The second tubular portion is pivotally connected to the distal end of the first tubular portion.

BRIEF DESCRIPTION OF THE DRAWINGS

The foregoing and other features of the present invention will become more apparent to one skilled in the art upon consideration of the following description of the invention and the accompanying drawings, in which:

FIG. 3 is a schematic end view showing the cannula of FIG. 1 in the expanded position;

FIG. 4 is a rollout view of a part of the cannula of FIG. 1;

FIG. 5 is a schematic sectional view of one position of the cannula of FIG. 1 during a surgical procedure;

FIG. 6 is an exploded schematic perspective view of another surgical cannula in accordance with the present invention, the cannula being shown in an expanded condition;

FIG. 7 is a schematic perspective view of the cannula of FIG. 6, the cannula being shown in a contracted condition;

FIG. 8 is an exploded schematic perspective view of still another surgical cannula in accordance with the present invention, the cannula being shown in an expanded condition;

FIG. 9 is a schematic sectional view of part of the cannula of FIG. 8;

FIG. 10 is a schematic end view, similar to FIG. 3, of part of another cannula in an expanded condition.

FIG. 11 is a schematic elevational view of a support apparatus in accordance with the present invention;

FIG. 12 is a schematic view taken along line 12-12 in FIG. 11;

FIG. 13 is a schematic view taken along line 13-13 in FIG. 11 showing part of the support apparatus of FIG. 11;

FIG. 18 is a schematic view taken along line 18-18 in FIG. 11 showing part of the support apparatus of FIG. 11;

FIG. 19 is a schematic perspective view of the support apparatus of FIG. 11;

FIG. 20 is a schematic perspective view of the support apparatus of FIG. 11 looking at the support apparatus from an angle different than FIG. 19;

FIG. 21 is a schematic perspective view of the support apparatus of FIG. 11 looking at the support apparatus from an angle different than FIGS. 19 and 20;

FIG. 22 is a sectional view taken approximately along line 22-22 of FIG. 14;

FIG. 23 is an enlarged view of a part of FIG. 22;

FIG. 24 is a schematic end view taken along line 24-24 in FIG. 15 with parts removed;

FIG. 25 is a view further illustrating parts shown in FIG. 15;

FIG. 26 is a sectional view taken approximately along line 26-26 of FIG. 25;

FIG. 27 is a schematic view showing part of the support apparatus of FIG. 11 with an associated known mechanical arm;

FIG. 28 is a schematic view of another feature of part of the support apparatus of FIG. 11;

FIG. 31 is an exploded schematic perspective view of part of the assembly of FIG. 29;

FIG. 32 is a schematic view of another fixation assembly attached to vertebrae of a patient;

FIG. 33 is a schematic view taken along line 33-33 of FIG. 32;

FIG. 34 is an exploded schematic perspective view of part of the assembly of FIG. 32;

FIG. 36 is a schematic sectional view of the position of another cannula during a surgical procedure in accordance with another feature of the present invention;

FIG. 37 is a schematic sectional view of positions of cannulae during a surgical procedure in accordance with still another feature of the present invention;

FIG. 39 is a schematic exploded view of part of a cutting tool used with a method in accordance with the present invention; and FIG. 40 is a schematic view of part of the cutting tool of FIG. 39.

DESCRIPTION OF A PREFERRED EMBODIMENT

Figure 1:
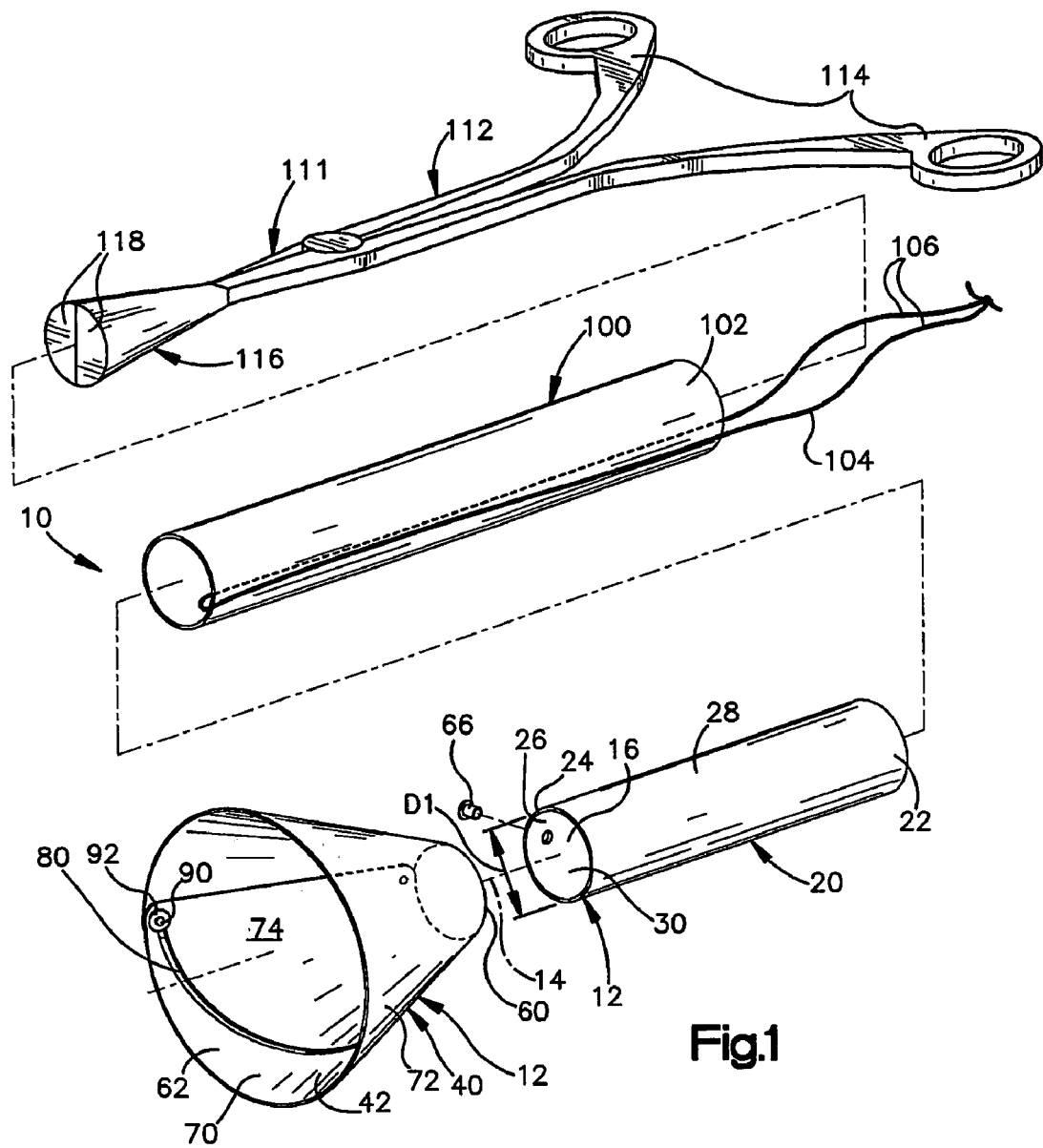
FIG. 1 is an exploded schematic perspective view of a surgical cannula constructed for use with the present invention, the cannula being shown in an expanded condition.

The present invention is directed to a method and apparatus for use in a surgical procedure, and particularly for fixing together the vertebrae of a patient at a surgical site. The method involves the use of a cannula, an adjustable support for the cannula, surgical instruments, and a viewing device.

FIGS. 1-5 illustrate one suitable cannula 10 constructed for use in a method in accordance with the present invention. The cannula 10 is a tubular structure 12 centered on an axis 14. The tubular structure 12 defines a passage 16 through the cannula 10. Surgical instruments may be inserted into the body during surgery through the passage 16.

The tubular structure 12 comprises a first tubular portion 20 and a second tubular portion 40 attached to the first tubular portion. The first tubular portion 20 is preferably made of a length of stainless steel tubing, but could alternatively be made of another suitable material such as a radiolucent material. The first tubular portion 20 has a proximal end 22 and a distal end 24. Parallel cylindrical inner and outer surfaces 26 and 28, respectively, extend between the ends 22, 24 of the first tubular portion 20. The inner surface 26 defines a first passage portion 30 of the passage 16 through the cannula 10. The first passage portion 30 has a diameter D1 that is preferably in the range from 10 mm to 30 mm (or approximately 0.4 to 1.2 inches).

The inner surface 26 may have a non-reflective coating. The non-reflective coating reduces glare on any video image produced by a video camera inserted through the passage 16. Alternatively, the inner surface 26 may not have the coating.

The second tubular portion 40 of the tubular structure 12 is attached to the distal end 24 of the first tubular portion 20. The second tubular portion 40 is preferably made from stainless steel, but could alternatively be made from another suitable material such as a radiolucent material.

As best seen in the rollout view of FIG. 4, the second tubular portion 40 comprises an arcuate segment 42 of sheet stock. The arcuate segment 42 includes first and second arcuate edges 44, 46, respectively, and first and second planar edges 48, 50, respectively. The first and second planar edges 48, 50 are rolled in an overlapping manner to form the tubular configuration of the second tubular portion 40.

When the second tubular portion 40 has been rolled into its tubular configuration, the first and second arcuate edges 44, 46 define oppositely disposed first and second ends 60, 62 (FIGS. 1 and 2), respectively, of the second tubular portion. The first and second ends 60, 62 are connected by a central portion 64. The first end 60 of the second tubular portion 40 is attached to the distal end 24 of the first tubular portion 20 by a single fastener, such as a rivet 66. The rivet 66 extends through two aligned apertures 68 (FIG. 4) at the first end 60 of the second tubular portion 40. The first end 60 of the second tubular portion 40 is pivotable about the rivet 66.

The second tubular portion 40 includes parallel inner and outer surfaces 70, 72 (FIGS. 1 and 2), respectively, extending between the first and second ends 60, 62. The inner surface 70 defines a second passage portion 74 of the passage 16 through the cannula 10 that extends as a continuation of the first passage portion 30 of the first tubular portion 20. The inner surface 70 may optionally have a non-reflective coating (not shown).

An arcuate slot 80 is formed in the second tubular portion 40 and extends between the inner and outer surfaces 70, 72 of the second tubular portion. The arcuate slot 80 extends along a curvilinear path in the central portion 64 of the second tubular portion 40 toward the second end 60 of the second tubular portion. The arcuate slot 80 has a first terminal end 82 located in the central portion 64 of the second tubular portion 40. A second terminal end 84 of the arcuate slot 80 is located adjacent the intersection of the second arcuate edge 46 and the first planar edge 48 of the arcuate segment 42.

A guide pin 90 is attached to the inner surface 70 of the second tubular portion 40 adjacent the intersection of the second arcuate edge 46 and the second planar edge 50. In the tubular configuration of the second tubular portion 40, the guide pin 90 is located in the arcuate slot 80 and is movable along the curvilinear path of the arcuate slot. A washer 92 is secured at an inner end of the guide pin 90 to retain the guide pin in the arcuate slot 80.

Figure 2:
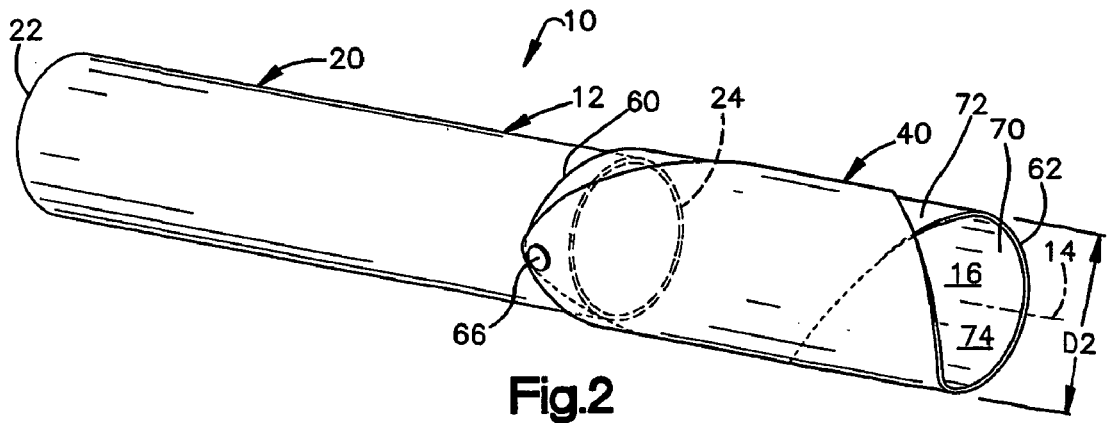
FIG. 2 is a schematic perspective view of the cannula of FIG. 1 with parts removed for clarity, the cannula being shown in a contracted condition.
Figure 14:
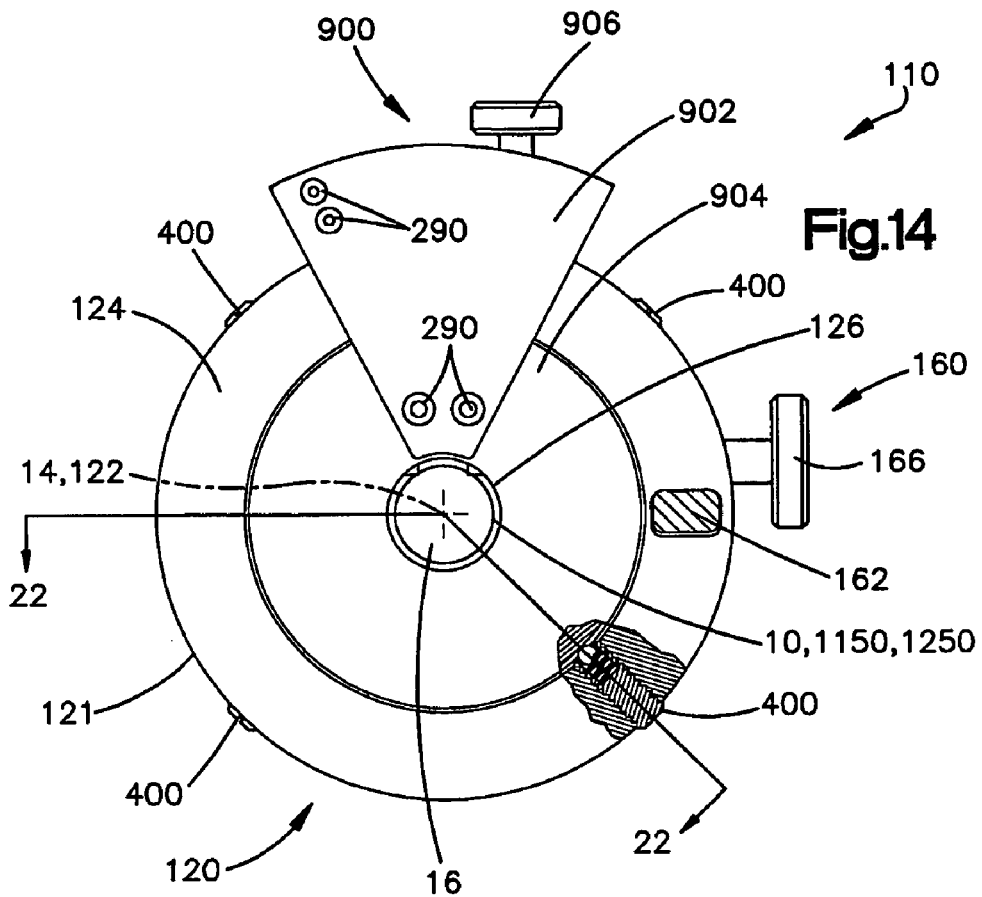
FIG. 14 is a schematic view taken along line 14-14 in FIG. 11 showing part of the support apparatus of FIG. 11.

The second tubular portion 40 of the tubular structure 12 is expandable from a contracted condition shown in FIG. 2 to an expanded condition shown in FIG. 1. In the contracted condition, the guide pin 90 is located at the first terminal end 82 of the arcuate slot 80 in the second tubular portion 40 and the second passage portion 74 defined by the second tubular portion is generally cylindrical in shape. The second passage 74 has a generally constant diameter D2 (FIGS. 2 and 3) that is approximately equal to the diameter D1 of the first tubular portion 20. Thus, the cross-sectional area of the second passage portion 74 at the second end 62 of the second tubular portion 40, which is a function of the diameter D2, is approximately the same as the cross-sectional area at the first end 60 of the second tubular portion and is approximately the same as the cross-sectional area of the first passage portion 30 in the first tubular portion 20.

In the expanded condition, the guide pin 90 is located at the second terminal end 84 of the arcuate slot 80 in the second tubular portion 40 and the second tubular portion has a generally conical configuration. At the second end 62 of the second tubular portion 40, the second passage portion 74 has a diameter D3 (FIG. 3) that is larger then the diameter D2 of the second passage portion at the first end 60 (typically 14 mm to as large as 60 mm or 0.6 to 2.4 inches). Preferably, the diameter D3 of the second passage portion 74 at the second end 62 of the second tubular portion is 40% to 90% greater than the diameter D1 of the second passage portion at the first end 60. Thus, in the expanded condition, the cross-sectional area of the second passage portion 74 at the second end 62 of the second tubular portion 40, which is function of the diameter D3, is 16% to 81% greater than the cross-sectional area of the second passage portion at the first end 60 of the second tubular portion. In the expanded condition, the cross-sectional area of the second passage portion 74 at the second end 62 of the second tubular portion 40 may be large enough to overlie a major portion of at least two, and as many as three, adjacent vertebrae.

The cannula 10 includes an outer layer 100 (FIG. 1) for maintaining the second tubular portion 40 of the cannula in the contracted condition. It is contemplated that other suitable means for maintaining the second tubular portion 40 in the contracted condition may be employed. Preferably, the outer layer 100 comprises a section of plastic tubing 102 which is heat shrunk over both the first and second tubular portions 20, 40 to hold the second tubular portion in the contracted condition.

In addition, a loop of polyester string 104 for tearing the tubing 102 is wrapped around the tubing so that it extends both underneath, and on top of, the tubing. An outer end 106 of the string 104 extends beyond the tubing 102.

FIG. 1 shows an actuatable device 111 for expanding the second tubular portion 40 from the contracted condition to the expanded condition. Preferably, the actuatable device 111 comprises a manually operated expansion tool 112. The expansion tool 112 resembles a common pair of scissors and has a pair of legs 114 pivotally connected to one another. The expansion tool 112 includes a frustoconical end section 116 forming a pair of frustoconical halves 118. Each of the frustoconical halves 118 extends from a respective one of the legs 114 of the expansion tool 112. It is contemplated that other suitable means for expanding the second tubular portion 40 toward the expanded condition may be employed, such as an inflatable balloon (not shown).

During a typical endoscopic surgical procedure, the cannula 10 is inserted into the body of a patient in the contracted condition. The outer end 106 of the string 104 is then manually pulled on by a surgeon, nurse, or other technician. Pulling on the string 104 tears the tubing 102 most of the way along the tubing, thereby freeing the second tubular portion 40 for expansion. The tubing 102, in its torn condition, may remain attached or secured to the first tubular portion 20.

Next, the expansion tool 112 is inserted into the passage 16 in the cannula 10 until the frustoconical end section 114 is located at the second end 62 of the second tubular portion 40. The legs 114 of the expansion tool 112 are manually separated, causing the frustoconical halves 118 to separate. As the halves 118 separate, a radially outward directed force is exerted on the inner surface 70 of the second tubular portion 40 by the halves 118, causing the second tubular portion to expand toward the expanded condition. Under the force of the expanding expansion tool 112, the guide pin 90 slides from the first terminal end 82 of the arcuate slot 80 to the second terminal end 84 of the arcuate slot to permit the expansion of the second tubular portion 40. The expansion tool 112 can be rotated about the axis 14 to ensure that the second tubular portion 40 of the cannula 10 is completely expanded to the expanded condition. The expansion tool 112 is then collapsed and removed so that one or more surgical instruments (indicated schematically at 21 in FIG. 5) and a viewing element can be received through the cannula 10 and inserted into a patient's body 130. The expandable second tubular portion 40 of the cannula 10 provides a significantly larger working area for the surgeon inside the body 130 within the confines of the cannula. As a result, the simultaneous use of a number of surgical instruments (such as steerable instruments, shavers, dissectors, scissors, forceps, retractors, dilators, etc.) is possible with the expandable cannula 10.

The expanded second tubular portion 40 can dilate and locally retract and separate spinalis muscle and soft tissues from the vertebrae thereby creating an endoscopic operating field at the surgical site. This endoscopic operating field within the spinal muscles differs from arthroscopic, laparoscopic, or cystoscopic working spaces in that there is no physiologic space or defined tissue plane that can be insufflated with air or distended with fluid.

FIGS. 6-7 illustrate another suitable cannula 1150 constructed for use in a method in accordance with the present invention. The cannula 1150 includes a tubular structure 1152 centered on an axis 1154. The tubular structure 1152 defines a passage 1156 through the cannula 1150. Surgical instruments may be inserted into the body 130 during endoscopic surgery through the passage 1156.

The tubular structure 1152 (FIG. 6) comprises a first tubular portion 1160 and a second tubular portion 1180 attached to the first tubular portion. The first tubular portion 1160 is preferably made of a length of stainless steel tubing, but could alternatively be made of another suitable material such as a radiolucent material. The first tubular portion 1160 has a proximal end 1162 and a distal end 1164. Parallel cylindrical inner and outer surfaces 1166, 1168 extend between the ends 1162, 1164 of the first tubular portion 1160. The first tubular portion 1160 has a thickness measured perpendicular to the surfaces 1166, 1168 in the range of approximately 0.5 mm to approximately 1.0 mm (or 0.02 inches to 0.04 inches).

The inner surface 1166 defines a first passage portion 1170 of the passage 1156 through the cannula 1150. The first passage portion 1170 has a diameter d1 that is preferably in the range of 10 mm to 30 mm (or approximately 0.4 inches to 1.2 inches). The inner surface 1166 may have a non-reflective coating 1174. The non-reflective coating 1174 reduces glare on any video image produced by a video camera inserted through the passage 1156. Alternatively, the inner surface 1166 may not have the coating 1174.

The second tubular portion 1180 (FIG. 6) of the tubular structure 1152 is attached to the distal end 1164 of the first tubular portion 1160. The second tubular portion 1180 is preferably made from stainless steel, but could alternatively be made from another suitable material such as a radiolucent material.

The second tubular portion 1180 includes an arcuate segment 1182 of sheet stock. The arcuate segment 1182 includes first and second arcuate edges 1184, 1186. The arcuate segment 1182 also includes a first planar edge 1188 and a second planar edge (not shown) extending between the arcuate edges 1184, 1186. The first 1188 and second planar edges are rolled in an overlapping manner to form the tubular configuration of the second tubular portion 1180.

When the second tubular portion 1180 has been rolled into its tubular configuration, the first and second arcuate edges 1184, 1186 define oppositely disposed first and second ends 1200, 1202 of the second tubular portion. The first and second ends 1200, 1202 are connected by a central portion 1204. The first end 1200 of the second tubular portion 1180 is attached to the distal end 1164 of the first tubular portion 1160 by a suitable fastener, such as a screw 1206 and nut 1208 threaded onto the screw. Alternatively, the second tubular portion 1180 may be connected to the first tubular portion 1160 by a rivet. The screw 1206 extends through two aligned apertures 1240 at the first end 1200 of the second tubular portion 1180. The first end 1200 of the second tubular portion 1180 is pivotable about the screw 1206.

The second tubular portion 1180 includes parallel inner and outer surfaces 1212, 1214 extending between the first and second ends 1200, 1202. The inner surface 1212 defines a second passage portion 1216 of the passage 1156 through the cannula 1150 that extends as a continuation of the first passage portion 1170 in the first tubular portion 1160. The second tubular portion 1180 has a thickness measured perpendicular to the surfaces 1212, 1214 in the range of approximately 0.075 mm to 0.15 mm (or 0.003 inches to 0.006 inches). The inner surface 1212 has a non-reflective coating 1218. The non-reflective coating 1218 reduces glare on any video image produced by a camera inserted through the passage 1156. Alternatively, the inner surface 1212 may not have the coating 1218.

An arcuate slot 1220 (FIG. 6) is formed in the second tubular portion 1180 and extends between the inner and outer surfaces 1212, 1214 of the second tubular portion. The arcuate slot 1220 extends along a curvilinear path in the central portion 1204 of the second tubular portion 1180 toward the end 1184 of the second tubular portion. The arcuate slot 1220 has a first terminal end (not shown) located in the central portion 1204 of the second tubular portion 1180. A second terminal end 1224 of the arcuate slot 1220 is located adjacent the intersection of the second arcuate edge 1186 and the planar edge 1188 of the arcuate segment 1182.

A guide member or screw 1230 is attached to the inner surface 1212 of the second tubular portion 1180 adjacent the intersection of the second arcuate edge 1186 and the second planar edge (not shown). Alternatively, a guide pin could be used instead of the screw 1230. In the tubular configuration of the second tubular portion 1180, the guide member 1230 is located in the arcuate slot 1220 and is movable along the curvilinear path of the arcuate slot.

The second tubular portion 1180 of the tubular structure 1152 is expandable from a contracted condition, shown in FIG. 7, to an expanded condition, shown in FIG. 6. In the contracted condition (FIG. 7), the guide member 1230 is located at the first terminal end (not shown) of the arcuate slot 1220 in the second tubular portion 1180 and the second passage portion 1216 defined by the second tubular portion is generally cylindrical in shape. The second passage 1216 has a generally constant diameter d2 that is approximately equal to the diameter d1 of the first tubular portion 1160. Thus, the cross-sectional area of the second passage portion 1216 at the second end 1202 of the second tubular portion 1180, which is a function of the diameter d2, is approximately the same as the cross-sectional area at the first end 1200 of the second tubular portion and is approximately the same as the cross-sectional area of the first passage portion 1170 in the first tubular portion 1160.

In the expanded condition (FIG. 6), the guide member 1230 is located at the second terminal end 1224 of the arcuate slot 1220 in the second tubular portion 1180 and the second tubular portion has a generally conical configuration. At the second end 1202 of the second tubular portion 1180, the second passage portion 1216 has a diameter d3 that is larger than the diameter d2 of the second passage portion at the first end 1200. Preferably, the diameter d3 of the second passage portion 1216 at the second end 1202 of the second tubular portion is 40% to 90% greater than the diameter d2 of the second passage portion at the first end 1200. Thus, in the expanded condition, the cross-sectional area of the second passage portion 1216 at the second end 1202 of the second tubular portion 1180, which is function of the diameter d3, is greater than the cross-sectional area of the second passage portion at the first end 1200 of the second tubular portion.

The cannula 1150 includes an outer member (not shown) for maintaining the second tubular portion 1180 of the cannula in the contracted condition. It is contemplated that other suitable means for maintaining the second tubular portion 1180 in the contracted condition may be employed. Preferably, the outer member may be similar to the layer 100 shown in FIG. 1 and include a section of plastic tubing which is heat shrunk over both the first and second tubular portions 1160, 1180 to hold the second tubular portion 1180 in the contracted condition. In addition, a loop of nylon string (not shown) for tearing the tubing may be wrapped around the tubing so that it extends both underneath and on top of the tubing. An outer end of the string may extend beyond the tubing.

During an endoscopic surgical procedure, the cannula 1150 is inserted through an incision into the body 130 of a patient in the contracted condition. The second tubular portion 1180 is inserted inside the body 130. The first tubular portion 1160 is inserted into the incision so that the first tubular portion extends from an exterior of the body 130 to inside the body.

The outer end of the string may then be manually pulled on by a surgeon, nurse, or other technician. Pulling on the string tears the tubing that is then removed from the cannula 1150. With the tubing removed, the second tubular portion 1180 of the cannula 1150 is thereby released for expansion toward the expanded condition.

Next, the expansion tool 112, shown in FIG. 1, may be inserted into the passage 1156 in the cannula 1150 until the frustoconical end section 114 is located at the second end 1202 of the second tubular portion 1180. The legs 114 of the expansion tool 112 are manually separated, causing the frustoconical halves 118 to separate. As the halves 118 separate, a radially outwardly directed force is exerted on the inner surface 1212 of the second tubular portion 1180 by the halves 118, causing the second tubular portion to expand toward the expanded condition. Under the force of the expanding expansion tool 112, the guide member 1230 slides from the first terminal end of the arcuate slot 1220 to the second terminal end 1224 of the arcuate slot to permit the expansion of the second tubular portion 1180. The expansion tool 112 can be rotated about the axis 1154 to ensure that the second tubular portion 1180 of the cannula 1150 is completely and uniformly expanded to the expanded condition. The expansion tool 112 is then collapsed and removed so that one or more surgical instruments and a viewing element can be received through the cannula 1150 and inserted into a patient's body 130.

The thickness of the second tubular portion 1180 allows the second tubular portion to deform as the second tubular portion expands. As the second tubular portion 1180 expands and engages tissue in the body 130, the tissue resists expansion of the second tubular portion. The second tubular portion 1180 may deform slightly to prevent the second tubular portion from being damaged while expanding. Because of this deformation, the expanded second tubular portion 1180 may be elliptical-conical in shape.

The expandable second tubular portion 1180 of the cannula 1150 provides a significantly larger working area for the surgeon inside the body 130 within the confines of the cannula. As a result, the simultaneous use of a number of endoscopic surgical instruments, including but not limited to steerable instruments, shavers, dissectors, scissors, forceps, retractors, dilators, and video cameras, is made possible by the expandable cannula 1150.

FIGS. 8-9 illustrate still another suitable cannula 1250 constructed for use in a method in accordance with the present invention. In the cannula 1150 in FIGS. 6-7, the tubular portions 1160 and 1180 are connected by a screw 1206 and nut 1208 and the guide member is a screw 1230. In the cannula 1250, the tubular portions are connected by a rivet and the guide member is a rivet. The cannula 1250 is similar to the cannula 1150 shown in FIGS. 6-7 with regard to the other features. Accordingly, only the rivets will be described in detail.

The cannula 1250 (FIG. 8) includes a tubular structure 1252 centered on an axis 1254. The tubular structure 1252 defines a passage 1256 through the cannula 1250. The tubular structure 1252 includes a first tubular portion 1260 and a second tubular portion 1280 attached to the first tubular portion. The first tubular portion 1260 has a proximal end 1262 and a distal end 1264. Parallel cylindrical inner and outer surfaces 1266 and 1268 extend between the ends 1262, 1264 of the first tubular portion 1260. The inner surface 1266 defines a first passage portion 1270 of the passage 1256 through the cannula 1250. The inner surface 1266 may optionally have a non-reflective coating (not shown).

The second tubular portion 1280 (FIG. 8) of the tubular structure 1252 is attached to the distal end 1264 of the first tubular portion 1260. The second tubular portion 1280 includes an arcuate segment 1282 of sheet stock. The arcuate segment 1282 includes first and second arcuate edges 1284, 1286. The arcuate segment 1282 also includes a first planar edge 1288 and a second planar edge (not shown) extending between the arcuate edges 1284, 1286. The first 1288 and second planar edges are rolled in an overlapping manner to form the tubular configuration of the second tubular portion 1280.

When the second tubular portion 1280 has been rolled into its tubular configuration, the first and second arcuate edges 1284, 1286 define oppositely disposed first and second ends 1300, 1302 of the second tubular portion. The first and second ends 1300, 1302 are connected by a central portion 1304. The first end 1300 of the second tubular portion 1280 is attached to the distal end 1264 of the first tubular portion 1260 by a rivet 1306. The rivet 1306 extends through two aligned apertures 1340 at the first end 1300 of the second tubular portion 1280. The first end 1300 of the second tubular portion 1280 is pivotable about the rivet 1306.

The rivet 1306 (FIGS. 8 and 9) has a first portion 1308 and a second portion 1310. The first portion 1308 has a shaft 1312 extending from a head 1314. The shaft 1312 extends through the apertures 1340 in the tubular portion 1280 and the head engages the inner surface 1266 of the first tubular portion 1260. A generally cylindrical opening 1316 extends through the shaft 1312 and the head 1314.

The second portion 1310 of the rivet 1306 has a shaft 1318 extending from a head 1320. The shaft 1318 extends into the opening 1316 in the first portion 1308 of the rivet 1306 and the head 1320 engages the second tubular portion 1280. The shaft 1318 of the second portion 1310 extends into the opening 1316 in the first portion 1308 to connect the first and second portions of the rivet 1306 and pivotally connect the second tubular portion 1280 to the first tubular portion 1260.

The second tubular portion 1280 (FIG. 8) includes parallel inner and outer surfaces 1322, 1324 extending between the first and second ends 1300, 1302. The inner surface 1322 defines a second passage portion 1326 of the passage 1256 through the cannula 1250 that extends as a continuation of the first passage portion 1270 in the first tubular portion 1260. The inner surface 1322 may optionally have a non-reflective coating (not shown).

An arcuate slot 1330 is formed in the second tubular portion 1280 and extends between the inner and outer surfaces 1322, 1324 of the second tubular portion. The arcuate slot 1330 extends along a curvilinear path in the central portion 1304 of the second tubular portion 1280 toward the end 1284 of the second tubular portion. The arcuate slot 1330 has a first terminal end (not shown) located in the central portion 1304 of the second tubular portion 1280. A second terminal end 1334 of the arcuate slot 1330 is located adjacent the intersection of the second arcuate edge 1286 and the first planar edge 1288 of the arcuate segment 1282.

A rivet 1336 is attached to the inner surface 1322 of the second tubular portion 1280 adjacent the intersection of the second arcuate edge 1286 and the second planar edge (not shown). Alternatively, a guide pin may be used instead of the rivet 1336. In the tubular configuration of the second tubular portion 1280, the rivet 1336 is located in the arcuate slot 1330 and is movable along the curvilinear path of the arcuate slot. A washer 1338 retains the rivet 1336 in the arcuate slot 1330.

The rivet 1336 is generally similar to the rivet 1306 and, therefore, will not be described in detail. The rivet 1336 has a first portion 1342 and a second portion 1344. The first portion 1342 has a shaft 1346 extending from a head 1348. The shaft 1346 extends through the slot 1330 and the head 1348 engages the washer 1338. A cylindrical opening 1350 extends through the shaft 1346 and the head 1348.

The second portion 1344 of the rivet 1336 has a shaft 1352 extending from a head 1354. The shaft 1352 extends into the opening 1350 in the first portion 1342 of the rivet 1336 and the head 1354 engages the outer surface 1324 of the second tubular portion 1280. The shaft 1352 extends into the opening 1350 to connect the first portion 1342 of the rivet 1336 to the second portion 1344.

The second tubular portion 1280 of the tubular structure 1252 is expandable from a contracted condition to an expanded condition, shown in FIG. 8. In the contracted condition the rivet 1336 is located at the first terminal end (not shown) of the arcuate slot 1330 in the second tubular portion 1280 and the second passage portion 1326 defined by the second tubular portion is generally cylindrical in shape. The second passage portion 1326 has a generally constant diameter that is approximately equal to the diameter of the first tubular portion 1260. Thus, the cross-sectional area of the second passage portion 1326 at the second end 1302 of the second tubular portion 1280 is approximately the same as the cross-sectional area at the first end 1300 of the second tubular portion and is approximately the same as the cross-sectional area of the first passage portion 1270 in the first tubular portion 1260.

In the expanded condition (FIG. 8), the rivet 1336 is located at the second terminal end 1334 of the arcuate slot 1330 in the second tubular portion 1280 and the second tubular portion has a generally conical configuration. At the second end 1302 of the second tubular portion 1280, the second passage portion 1326 has a diameter that is larger than the diameter of the second passage portion at the first end 1300. Thus, in the expanded condition, the cross-sectional area of the second passage portion 1326 at the second end 1302 of the second tubular portion 1280 is greater than the cross-sectional area of the second passage portion at the first end 1300 of the second tubular portion.

During a typical endoscopic surgical procedure, the cannula 1250 is inserted through an incision into the body 130 of a patient in the contracted condition. The second tubular portion 1280 is inserted inside the body 130. The first tubular portion 1260 is inserted into the incision so that the first tubular portion extends from an exterior of the body 130 to inside the body.

Restraint tubing (not shown) is removed from the cannula 1250 by a surgeon, nurse or other technician. With the tubing removed, the second tubular portion 1280 of the cannula 1250 is thereby released for expansion toward the expanded condition. Next, the expansion tool 112, shown in FIG. 1, is inserted into the passage 1256 in the cannula 1250 until the frustoconical end section 114 is located at the second end 1302 of the second tubular portion 1280. The legs 114 of the expansion tool 112 are manually separated, causing the frustoconical halves 118 to separate also. As the halves 118 separate, a radially outwardly directed force is exerted on the inner surface 1312 of the second tubular portion 1280 by the halves 118, causing the second tubular portion to expand toward the expanded condition. Under the force of the expanding expansion tool 112, the rivet 1336 slides from the first terminal end of the arcuate slot 1330 to the second terminal end 1334 of the arcuate slot to permit the expansion of the second tubular portion 1280. The expansion tool 112 is then collapsed and removed so that one or more surgical instruments and a viewing element can be received through the cannula 1250 and inserted into a patient's body 130.

The expandable second tubular portion 1280 of the cannula 1250 provides a significantly larger working area for the surgeon inside the body 130 within the confines of the cannula. As a result, the simultaneous use of a number of endoscopic surgical instruments, including but not limited to steerable instruments, shavers, dissectors, scissors, forceps, retractors, dilators, and video cameras, is made possible by the expandable cannula 1250.

As viewed in FIG. 10, a second tubular portion 1040 of the cannulae 10, 1150, and/or 1250 may be elliptical in shape in order to provide access to a larger area. The longitudinal dimension D4 of the second portion 1040 may expand to as much as 65 mm (or 2.6 inches) from a contracted condition (not shown).

FIGS. 11-28 illustrate one suitable support apparatus 110 for use in a method in accordance with the present invention. The support apparatus 110 includes a first support 120, a second support 140, a first adjustment mechanism 160, a second adjustment mechanism 180, and a third adjustment mechanism 900.

As viewed in FIGS. 2 and 22, the first support 120 is associated with the cannula 10, 1150, or 1250 (hereinafter only the cannula 10 will be referred to with respect to the support apparatus 110) and has a circular perimeter 121. The perimeter 121 has a center 122 located on the axis 14. The first support 120 comprises a circular platform, or disk 124, which has a circular opening 126 in the central area of the disk 124 for receiving the proximal end 22 of the cannula 10. The circular opening 126 has a center located on the axis 14. The proximal end 22 of the cannula 10 can be easily inserted into, and removed from, the opening 126. The disk 124 has a projection portion 120a, which is located adjacent the perimeter 121 of the disk 124. The disk 124 has an upper circular surface area 124a, which surrounds the opening 126.

As viewed in FIG. 20, the second support 140 supports a viewing device 200 including a camera head 201 and an endoscope 202 with a rod and lens assembly 203, herein referred to as a viewing element, extending down through the passage 16 of the cannula 10. The second support 140 includes a body 142 having an opening 144 through which the viewing device 200 extends and a clamp 146 for clamping the viewing device 200 to the body 142 in the opening 144. The clamp 146 includes a threaded set screw 148 for securing the viewing device 200 to the body 142. The set screw 148 has a manually rotatable knob 148a and a stem threaded into the body 142. When rotated, the screw 148 moves axially relative to the body 142 to clamp (or release) the viewing device 200 depending on the direction of rotation of the screw 148.

The body 142 of the second support 140 further includes two extension arms 151, 152 (FIG. 13) for supporting the endoscope 202. Each extension arm 151, 152 includes a threaded bore for receiving a resilient detent member, or ball plunger 400.

As viewed in FIGS. 22 and 23, a ball plunger 400 is illustrated at another location in the support apparatus 110. Each ball plunger 400, including those in the extension arms 151, 152, has an externally threaded tubular body 402 with a cylindrical cavity 404 located therein. The cavity 404 houses a projection 406 and a coiled spring 408. The projections 406 of the two ball plungers 400 of the extension arms 151, 152 are spherical detent members 420 in the form of balls (not shown). The spring 408 urges each projection 406 against a lip portion 409 of the body 402. The lip portion 409 is located at one end of the cavity 404. As shown in FIG. 19, the other ball plungers 400 of the apparatus 10 have projections 406 with hemispherical extensions 420 and shoulder portions 422.

As viewed in FIG. 20, the endoscope 202 has corresponding hemispherical recesses (not shown) for receiving the spherical detent members (balls) of the ball plungers 400 which are located in extension arms 151, 152. As the endoscope 202 is inserted between the extension arms 151, 152, the springs 408 will compress in each ball plunger 400 in each extension arm 151, 152 and the spherical detent members will move inward of each cavity 404 and then spring back into the hemispherical recesses in the endoscope 202. The entire viewing device 200 will thus be secured between the extension arms 151, 152, but may be removed by overcoming the biasing force of the spherical detent members of each ball plunger 400 in the extension arms 151, 152.

The ball plunger 400 further includes a head portion 430 with a slot 432 for engaging a tool, such as a screwdriver. The ball plunger 400 may be threadedly adjusted within the threaded bore of either extension arm 151, 152 to alter the distance that the spherical detent member 420 projects away from the extension arms 151, 152 (toward each other). This distance, along with the stiffness of each spring 408, will determine the holding force by which the endoscope 202 is secured between the extension arms 151, 152.

The first adjustment mechanism 160 provides for relative axial adjustment of the cannula 10 and the first support 120 along the axis 14. The first adjustment mechanism 160 includes a first toothed rack member 162, a cannula gripper mechanism 164 fixedly connected to the first rack member 162, a first manually adjustable, rotatable knob 166 rotatably carried by the projection portion 120a of the first support 120, and a first gear member 165 (FIG. 17) rotatable by the first knob 166 and in meshing engagement with the teeth 163 of the first rack member. The first support 120 and, in particular, the projection portion 120a, rotatably carries the first gear member 165 (FIG. 17).

Figure 17:
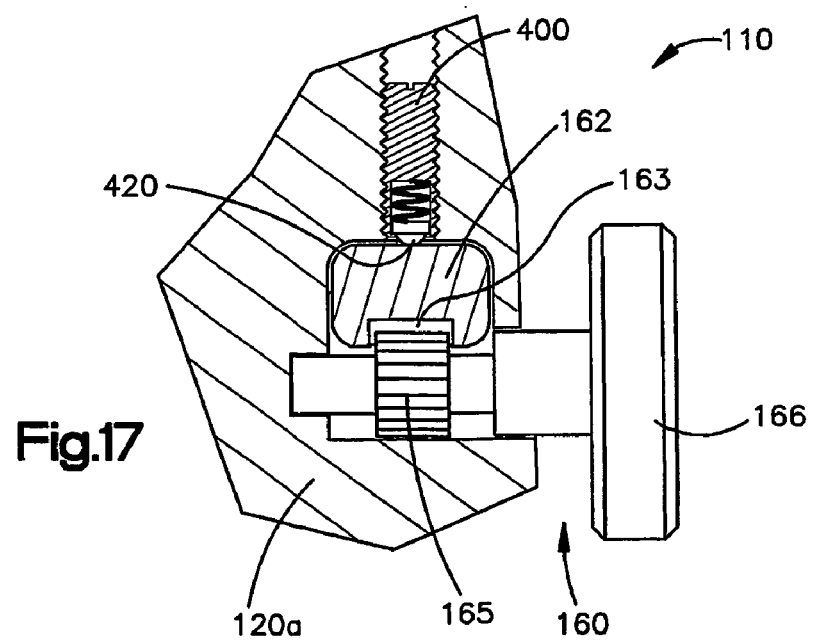
FIG. 17 is a schematic view taken along line 17-17 in FIG. 11 showing part of the support apparatus of FIG. 11.

The first rack member 162 is secured to slide axially within the first support 120 and the projection portion 120a by two ball plungers 400 (FIG. 17). One ball plunger 400 is tangentially threaded into a tapered, threaded bore (FIG. 12) in the perimeter 121 of the first support 120 and the other is tangentially threaded into a threaded bore in the projection portion 120a. The hemispherical extensions 420 thus frictionally engage a smooth portion (without teeth 163) of the first rack member 162 and bias the first rack member 162 against the first support 120 and the projection portion 120a. This biasing also maintains the engagement of the first rack member 162 and the first gear member 165 (FIG. 17).

Figure 15:
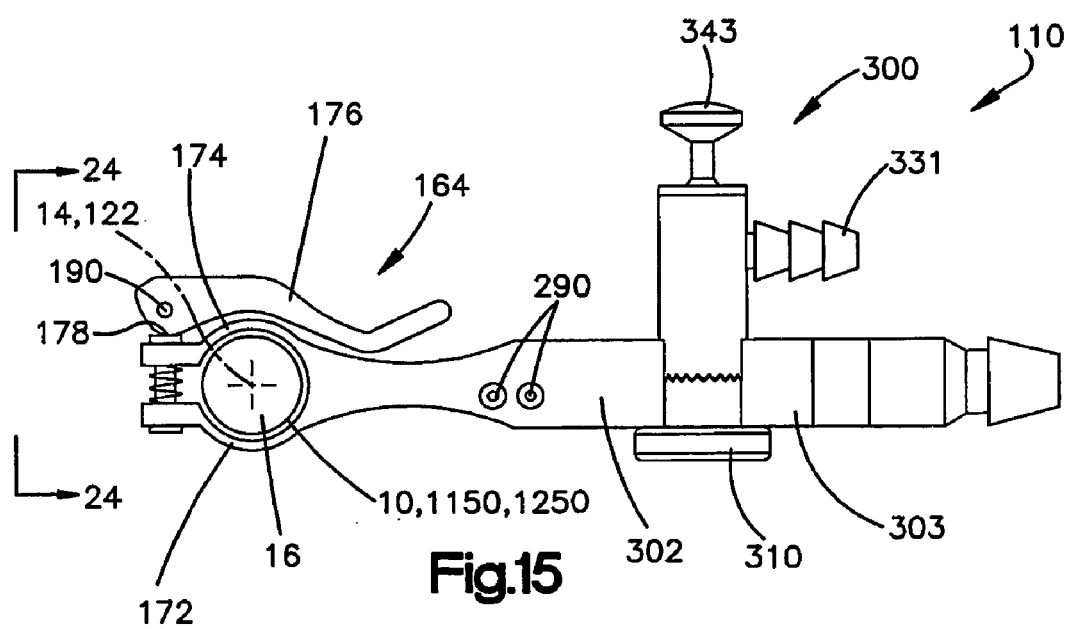
FIG. 15 is a schematic view taken along line 15-15 in FIG. 11 with parts removed.
Figure 16:
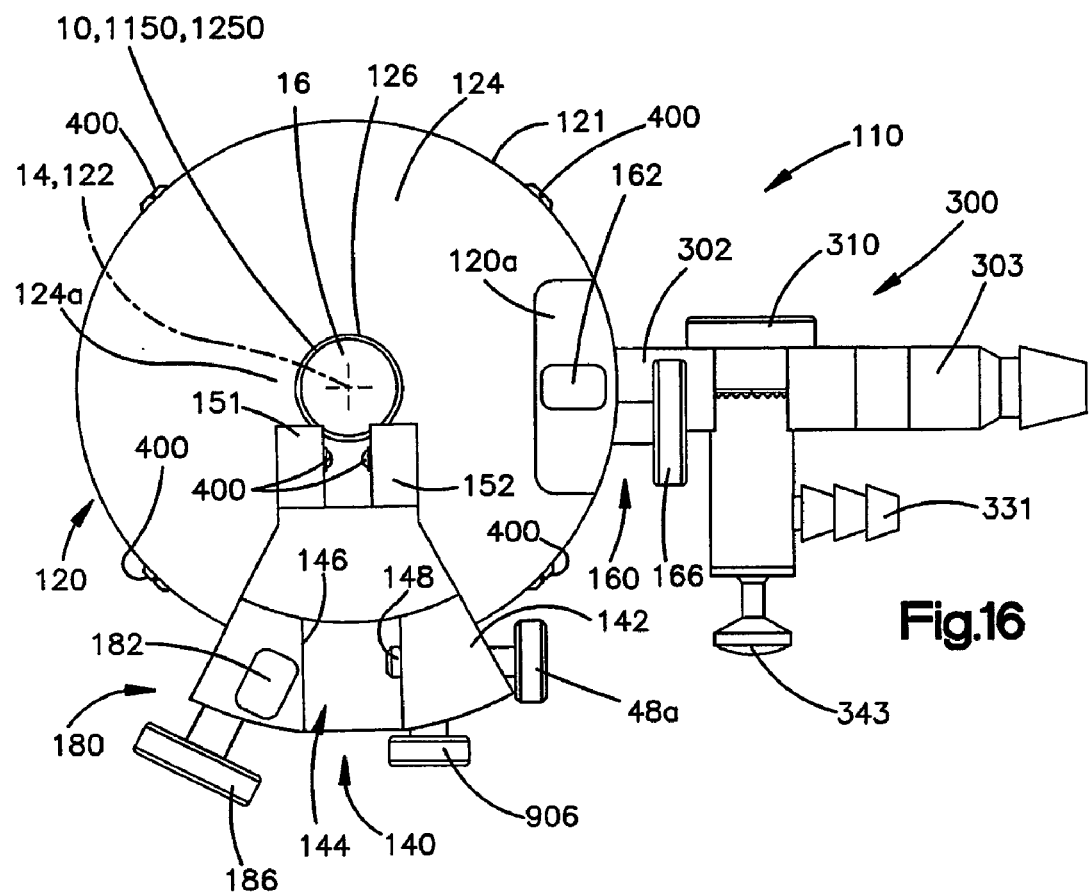
FIG. 16 is a schematic view taken along line 16-16 in FIG. 11.

As viewed in FIGS. 15 and 24, the cannula gripper mechanism 164 includes two gripper arms 172, 174 for clamping against the outer surface of the cannula 10, and a gripper actuating lever 176 for moving the arms 172, 174 into engagement with the outer surface of the cannula 10 and for releasing the arms 172, 174 from engagement with the cannula 10. References in this application to gripping the outer surface 28 of the cannula 10 are meant to also include the gripper arms 511, 512 engaging the tubing 102.

As viewed in FIG. 24, the cannula gripper mechanism 164 further includes a support pin 177, a coiled spring 188, a washer 189 with a bore (not shown), and a lock pin 190. The support pin 177 has a head 179, a shaft 180, and an oblong, or flat, end 181 that can mate with the bore in the washer 189. Other suitable structures could also be used.

During assembly, the coiled spring 188 is interposed between the arms 172, 174. The flat end 181 of the support pin 177 is inserted through a circular bore in the first clamp arm 172, through the coil of the spring 188, through a circular bore in the second arm 174, and through the bore in the washer 189. The flat end 181 of the support pin 177 is then inserted into a slot 176a in the lever 176. The lock pin 190 is inserted through a bore in the lever 176 and through a bore in the flat end 181 of the support pin 177 thereby securing the mechanism 164 together and allowing the lever 176 to rotate about the lock pin 190. A camming surface 178 on the lever 176 adjacent the washer 189 forces the arms 172, 174 together to grip the cannula 10 as the lever 176 is rotated clockwise (as viewed in FIG. 15). Counterclockwise rotation of the lever 176 allows the spring 188 to force the arms 172, 174 apart and releases the cannula 10 from the gripper mechanism 164.

When the gripper mechanism 164 is either gripping the cannula 10 or released from the cannula 10 and the knob 166 is rotated, the disk 124 and parts attached to the disk 124 will move along the axis 14 of the cannula 10 relative to the cannula 10. After the support apparatus 110 is initially lined up with the cannula 10, the viewing device 200 may be positioned on the support apparatus 110 and adjusted along the axis 14 by rotation of the first knob 166.

The second adjustment mechanism 180 provides axial adjustment of the first and second supports 20, 40 relative to each other along the axis 14. The second adjustment mechanism 180 includes a second toothed rack member 182 connected to the first support 120, a second manually adjustable, rotatable knob 186 rotatably carried by the body 142 of the second support 140, and a second toothed gear member 185 (FIG. 18) rotatable by the second knob 186 and in meshing engagement with the teeth 183 of the second rack member 182. The second support 140, and in particular, the body 142, rotatably carries the second gear member 185 (FIG. 18).

The body 142 of the second support 140 may have a notch 149 which can fit around part 902a of the third adjustment mechanism 900 and allow the lower surface of the body 142 to completely abut the disk 124 as the body 142 is brought into an axial position adjacent the disk 124.

The second rack member 182 is secured to slide axially within the second support 140 by a ball plunger 40.0 (FIG. 18). The ball plunger 400 is tangentially threaded into a threaded bore in the side of the notch 149 of the second support 140. The hemispherical extension 420 thus frictionally engages a smooth portion (without teeth 183) of the second rack member 182 and biases the second rack member 182 against the second support 140. The biasing also maintains the engagement of the second rack member 182 and the second gear member 185. Both sides of the notch 149 have tapered portions 149a, 149b for facilitating insertion of the ball plunger 400 into the threaded bore of the notch 149 of the second support 140. Rotation of the second knob 186 causes the body 142 and the viewing device 200 attached thereto to move relative to the cannula 10 and disk 124 along the axis 14.

The third adjustment mechanism 900 provides arcuate, circumferential adjustment of the second support 140 about the axis 14 relative to the first support 120. The third adjustment mechanism 900 includes a wedge-shaped support member 902 (FIG. 14) fixedly connecting the second rack member 182 to a ring member 904 that is rotatably supported by the first support 120 and rotatable about the axis 14 relative to the first support 120 (FIG. 22).

The third adjustment mechanism 900 further includes a third manually adjustable, rotatable knob 906 that is part of a set screw. The set screw is rotatably threaded into a projection portion 902a of the support member 902 and is engageable with the circular perimeter 121 of the disk 124 of the first support 120 to lock the support member 902 in an arcuate position relative to the first support 120 and the axis 14.

As viewed in FIGS. 22 and 23, the ring member 904 is supported within a cylindrical, open ended recess 905 of the first support 120. The recess 905 is concentric about the axis 14. The perimeter 904a of the ring member 904 has a groove 904b for engaging a plurality of ball plungers 400 (preferably four equally spaced apart) threaded into the first support 120. Each of these ball plungers 400 is similar in construction. Each ball plunger 400 is threaded radially into the perimeter 121 of the first support 120 to provide a hemispherical extension 420 extending into the recess 905 of the first support 120.

The ring member 904 thus is biasingly supported within the recess 905 of the first support 120 and can rotatably slide within the recess 905 about the axis 14. The ball plungers 400 operatively support the ring member 904 in the recess 905 of the first support 120. The ring member 904, along with the second support 140 and the second and third adjustment mechanisms 180, 900, can be easily removed from the recess 905 for cleaning, maintenance, etc. of the parts by overcoming the force applied by the ball plungers 400 to the ring member 904. When the third knob 906 is rotated to disengage the perimeter 121 of disk 124, the body 142 and parts connected thereto can be manually rotated about the axis 14. This causes the viewing device 200 to rotate about the axis 14 of the cannula 10 and enables the surgeon to view different parts of the surgical sight, as desired.

As viewed in FIG. 21, the fixed connections of the first rack member 162 to a support arm 300, the second rack member 182 to the wedge-shaped support member 902, and the support member 902 to the ring member 904 may be made by one or more suitable metal fasteners 290, such as rivets or bolts. The entire support apparatus 110 can be constructed from metal or any other suitable material having sufficient mechanical strength and durability. Certain parts may be made from materials permitting X-rays and other techniques for viewing the surgical sight (i.e., radiolucent parts). Other parts may also be made from non-magnetic materials to reduce electromagnetic interference (i.e., electromagnetic insulating parts).

As viewed in FIGS. 25-27, the gripper arms 172, 174 are a part of the support arm 300 for attaching the support apparatus 110 to a mechanical robotic arm 301. The support arm 300 includes an arm portion 302 that is formed integrally with the gripper arms 172, 174. The gripper arms 172, 174 are integrally constructed with the arm portion 302.

The support arm 300 also includes an arm portion 303. The arm portion 303 has an attaching structure 304, including a groove 305, which snaps into a socket in the mechanical arm 301. Detents of any suitable type and designated 306 in the mechanical arm 301, hold the arm portion 303 in position in the socket in the mechanical arm 301. The detents 306 may be controlled by external actuation levers (not shown) on the mechanical arm 301 for manually releasing the arm portion 303 from the mechanical arm 301.

The arm portions 302 and 303 are pivotally connected to each other by a fastener 310. The fastener 310 extends through an opening 311 in the arm portion 302 and threads into a threaded opening 312 in the arm portion 303. When the fastener 310 is released, the arm portions 302, 303 may pivot relative to each other about a pivot axis 314. The pivot axis 314 is centered on the axis of the fastener 310 and the axis of the threaded opening 312. When the fastener 310 is tightly screwed into the threaded opening 312, the arm portions 302, 303 are secured together against pivoting movement. When the fastener is released, the arm portions 303, 302 may pivot relative to each other about the axis 314.

The end of the arm portion 302, which is adjacent to the arm portion 303, has a convex surface 350, which is curved about the axis 314. The arm portion 303 has a concave surface 351, which is also curved about the axis 314. The surfaces 350, 351 move concentrically relative to each other when the arm portions 303, 302 pivot relatively about the axis 314.

The arm portion 303 has a set of teeth 320 which encircle the axis 314 and which project axially toward a set of teeth 321 on the arm portion 302. The teeth 321 project axially toward the teeth 320. The teeth 320 and the teeth 321 mesh with each other and provide a locking action so that the arm portions 302, 303 are positively locked against relative movement about axis 314 when the fastener 310 is tightly screwed into the opening 312. The teeth 320, 321 comprise a lock which blocks relative rotation of the arm portions 302, 303 about the axis 314. When the fastener 310 is loosened, the arm portions 302, 303 may be rotated relative to each other about the axis 314. Thus, the arm portions 302, 303 may pivot relative to each other to adjust the position of the support apparatus 110.

A cylindrical projection 325 is welded to the arm portion 303. Thus, the projection 325 and arm portion 303 are fixedly connected together. The projection 325 is centered on the axis 314 and contains a chamber 328.

As viewed in FIG. 27, the chamber 328 communicates with a fluid passage 329 in a male fluid connector 331. The male connector 331 attaches to a male connector 333 on the mechanical arm 301 by means of a flexible hose 392 so that the fluid passage 329 communicates with a fluid passage in the mechanical arm 301.

As viewed in FIG. 25, the chamber 328 is closed at its upper end by a cap 335. The cap 335 has an opening 336 centered on the axis 314. The opening 336 communicates with the chamber 328. A manually movable internal valve member 340 biasingly closes the opening and blocks the chamber 328 from communicating with the ambient air surrounding the support arm 300. The valve member 340 is connected to a stem 341, which is also centered on the axis 314. The stem 341 has a knob or button 343 on its end that may be manually depressed to move the stem 341 and valve member 340 downward into the chamber 328. When the stem 341 and valve member 340 are so moved, the chamber 328 is in communication with the ambient air surrounding the device due to the unblocking of the opening 336.

The mechanical arm 301 is a known device and is of the type generally disclosed in U.S. Pat. No. 4,863,133. The mechanical arm 301 is sold by Leonard Medical, Inc. 1464 Holcomb Road, Huntington Valley, Pa., 19006. The mechanical arm 301 includes relatively movable parts, which permit movement and adjustment of the support apparatus 110 in a variety in planes, directions, and orientations. The mechanical arm 301 permits easy movement when a vacuum is not applied to the arm 301. When a vacuum is applied to the arm 301, relative movement of the parts of the arm 301 is resisted, and therefore adjustment of the support apparatus 110 is difficult.

When the button 343 is depressed, the chamber 328 loses its vacuum and the pressure in the chamber 328 increases toward ambient pressure. The passage 329 communicates this pressure increase to the mechanical arm 301, and thus the parts of the mechanical arm 301 are free to move and allow for adjustment of the position of the support apparatus 110 by the surgeon.

Accordingly, when the surgeon uses the support apparatus 110, the support arm 300 is snapped into the socket of the mechanical arm 301 where it is held by the detent 306. The surgeon may then depress the button 343 and relatively move parts of the mechanical arm 301, as well as the support apparatus 110 into the position where the surgeon desires the support apparatus 110 to be. This position may be where the opening 126 in the disk 124 is aligned with the proximal end 16 of the cannula 10 that has been positioned in the patient's body with the distal end 24 of the cannula 10 being located in an incision in the body of the patient. The viewing device 200 may be mounted on the support apparatus 110, and the surgeon may make adjustments prior to and during the surgical procedure as desired, as described above.

As viewed in FIG. 28, the support apparatus 110 may include a second support with a fourth adjustment mechanism 500 for rotating the viewing device 200 about an axis 501 (FIG. 20) defined by the ball plungers 400 of the extension arms 151, 152 when set screw 148 is not clamping the viewing device 200 to the body 142. The axis 501 is offset from the axis 14 of the cannula 10 and perpendicular to the axis 14 of the cannula 10. Rotation of the viewing device 200 about axis 501 causes the endoscope 200 and the rod and lens assembly 203 to move perpendicular to the axis 14 of the cannula 10. This rotation will result in adjustment of the position of the rod and lens assembly 203 in a radial direction transverse to the axis 14.

The spring-loaded connections of the spherical detent members 420 of the ball plungers 400 and the hemispherical recesses of the endoscope 202 allow rotation about the axis 501 when the set screw 148 is released from clamping engagement of the viewing device 200.

The fourth adjustment mechanism 500 includes a threaded bore 510 in the second support 140 and an adjustable member 520 for moving (vertically as viewed in the Figs.) a part of the viewing device 200 about the axis 501. The adjustable member 520 has a rounded first end portion 522, a threaded middle portion 524, and a knurled second end portion 526, or knob. The bore 510 extends at an angle (as shown in FIG. 28) from a lower portion of the second support 140 up to the opening 144 in the clamp 146 of the second support 140.

The adjustable member 520 is rotated and threaded into the bore 510 and may be rotated until the first end portion 522 protrudes into the opening 144 of the second support 140. Accordingly, when the surgeon wishes to adjust the rod and lens assembly 203 (within the surgical sight) about the axis 501 and radially relative to the axis 14 of the cannula 10, the surgeon may loosen the connection of the set screw 148 with the viewing device 200 and rotate the adjustable member 520 by manually rotating knob 526 so that the first end portion 522 vertically extends farther or less into the opening 144. This adjustment will adjust the part of the viewing device 200 engaged by the clamp 146 along the axis 14, rotate the viewing device 200 about the axis 501, and cause the lens 203 at the surgical site to move transverse to the axis 14 of the cannula 10. This increases the area of the surgical site that the surgeon may view. When the adjustment is complete, the surgeon may tighten the set screw 148 and re-secure the viewing device 200 to the second support 140 of the support apparatus 110.

In accordance with one feature of the present invention, a method of securing two 601, 602 or three 1601, 1602, 1603 vertebrae together may include the insertion of a vertebral fixation assembly 620 through the cannula 10 and attachment of the vertebral fixation assembly 620 to the pedicles of two or three vertebrae (such as the L4, L5, and S1 vertebrae), as viewed in FIGS. 5 and 29-38.

Figure 29:
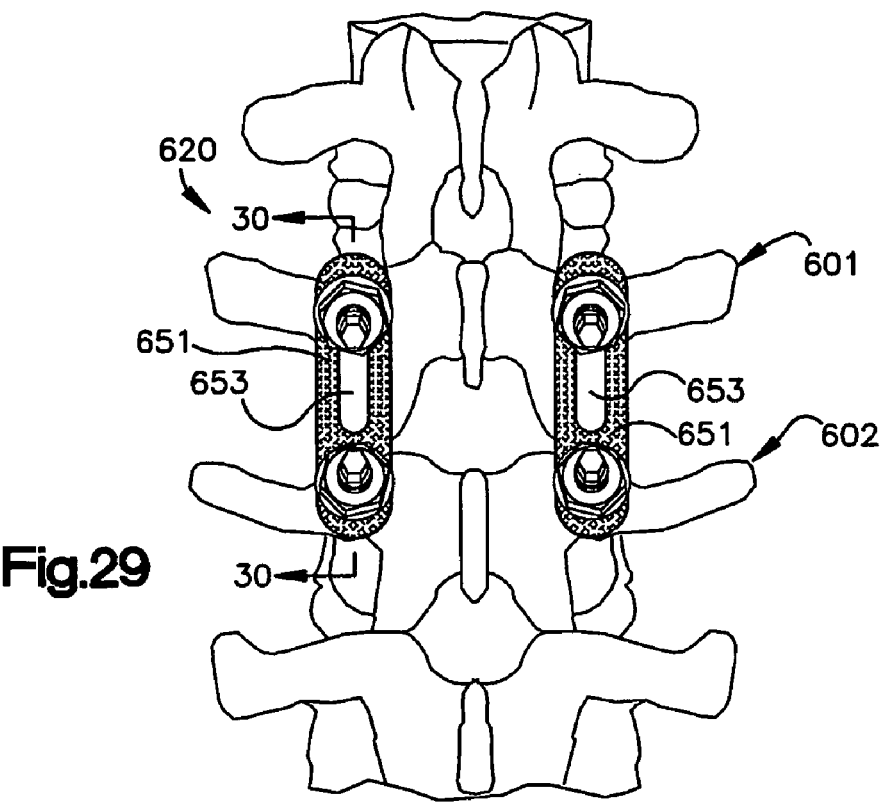
FIG. 29 is a schematic view of a fixation assembly attached to vertebrae of a patient.

The vertebral fixation assembly 620 may be of any suitable construction and is shown in FIGS. 29 and 32 as including four identical attachment devices 622. Each attachment device 622 includes a threaded fastener 624, or pedicle screw, placed in a pedicle of a vertebra 601 or 602, as viewed in FIGS. 30 and 33. The fastener 624 has a first threaded portion 626 with a first threaded diameter that threads into the pedicles of the vertebrae 601, 602 by screwing the fastener 624 into the pedicles of the vertebrae. The fastener 624 further includes a second threaded portion 628 with a second threaded diameter that may be less than the first threaded diameter. The second threaded portion 628 extends away from the vertebrae 601, 602.

A first hexagonal engagement surface 630, intermediate the first and second threaded portions 626, 628, allows gripping of the fastener 624 for screwing the fastener into the vertebrae 601, 602. A first convex engagement surface 632, adjacent the first hexagonal engagement surface 630 and the second threaded portion 628, projects away from the vertebrae 601, 602. A second hexagonal engagement surface 634 projects away from the second threaded portion 628 and allows further gripping of the fastener 624.

Each attachment device 622 further includes a first fixation washer 640 (FIGS. 31 and 34) that engages the first convex engagement surface 632. The first fixation washer 640 includes a first concave engagement surface 642 for abutting and slidingly engaging the first convex engagement surface 632 of the fastener 624.

The first fixation washer 640 further includes spikes 644, typically three, extending away from the vertebrae 601, 602. The spikes 644 of the first fixation washer 640 engage a lower knurled surface 652 of a vertebral fixation element 650 that in FIG. 29 is a spine plate (and FIG. 32 is a universal side block.

An upper knurled surface 654 of the fixation element 650 engages the spikes 664 of a second fixation washer 660 that is identical to the first fixation washer 640, but inverted, as viewed in FIGS. 31 and 34. A second convex engagement surface 672 of a threaded locking nut 670 abuts and slidingly engages the second concave engagement surface 662 of the second fixation washer 660 when the locking nut 670 is loosely threaded onto the second threaded portion 628 of the fastener 624.

Figure 30:
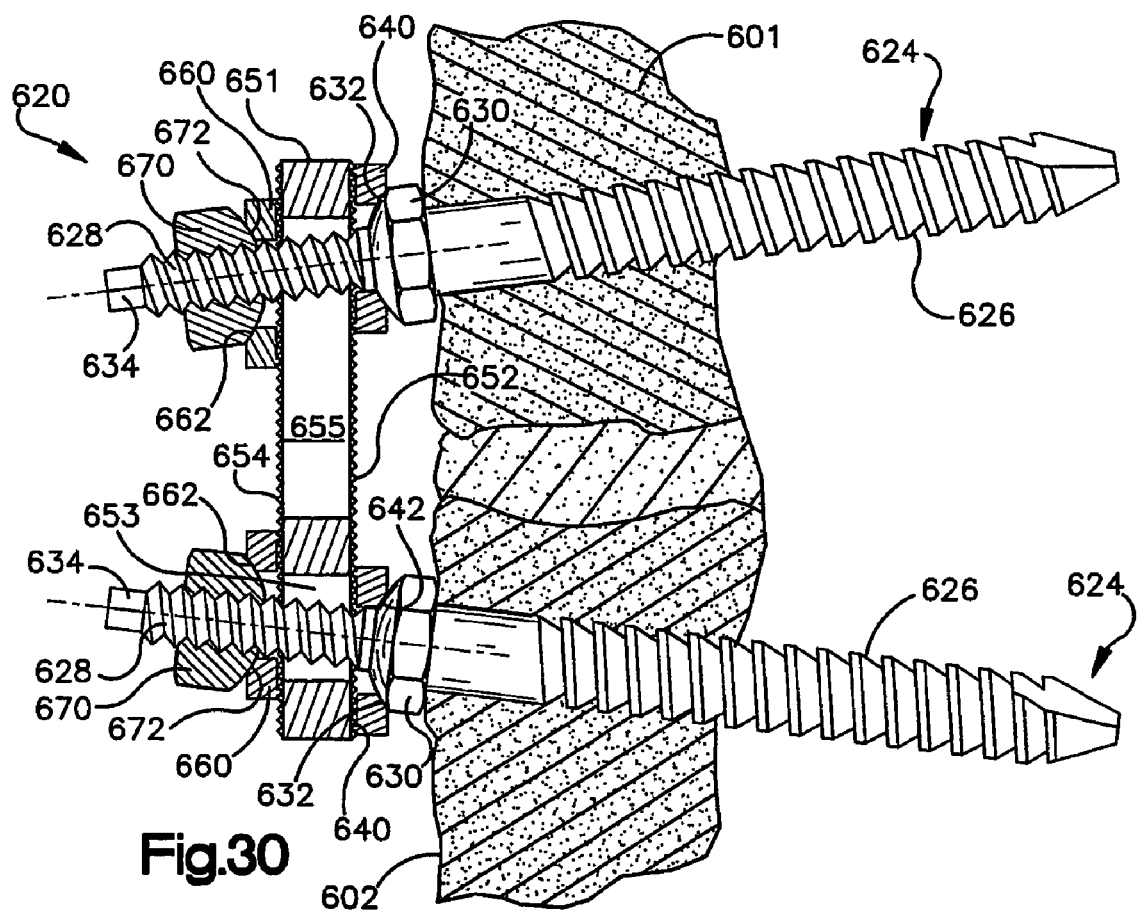
FIG. 30 is a schematic view taken along line 30-30 of FIG. 29.
Figure 35A:
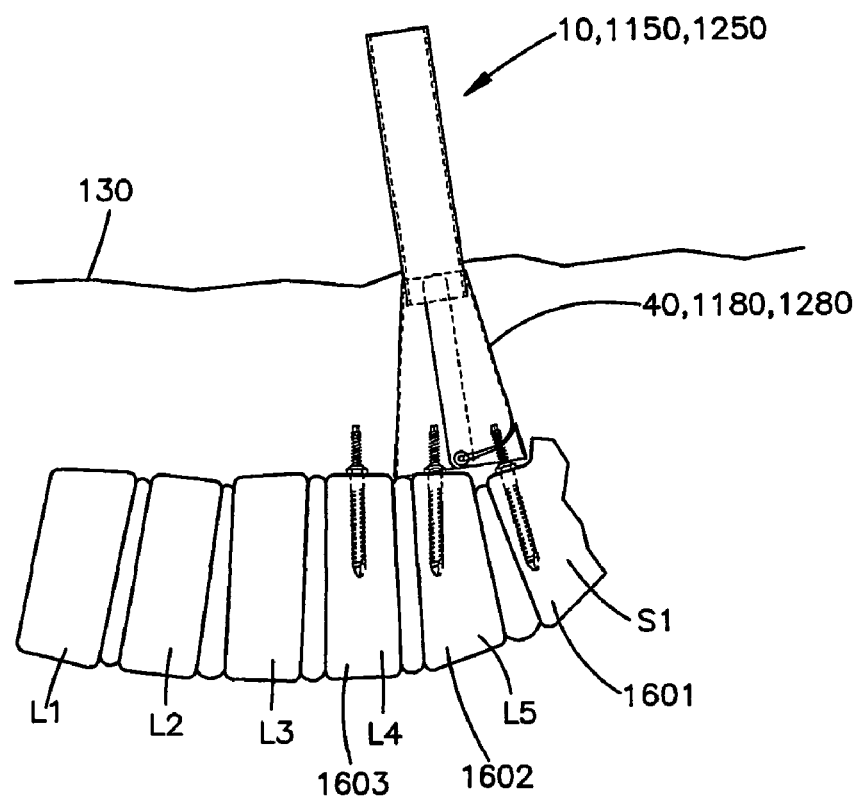
FIG. 35A is a schematic sectional view of one position of a cannula during a surgical procedure in accordance with one feature of the present invention.
Figure 35B:
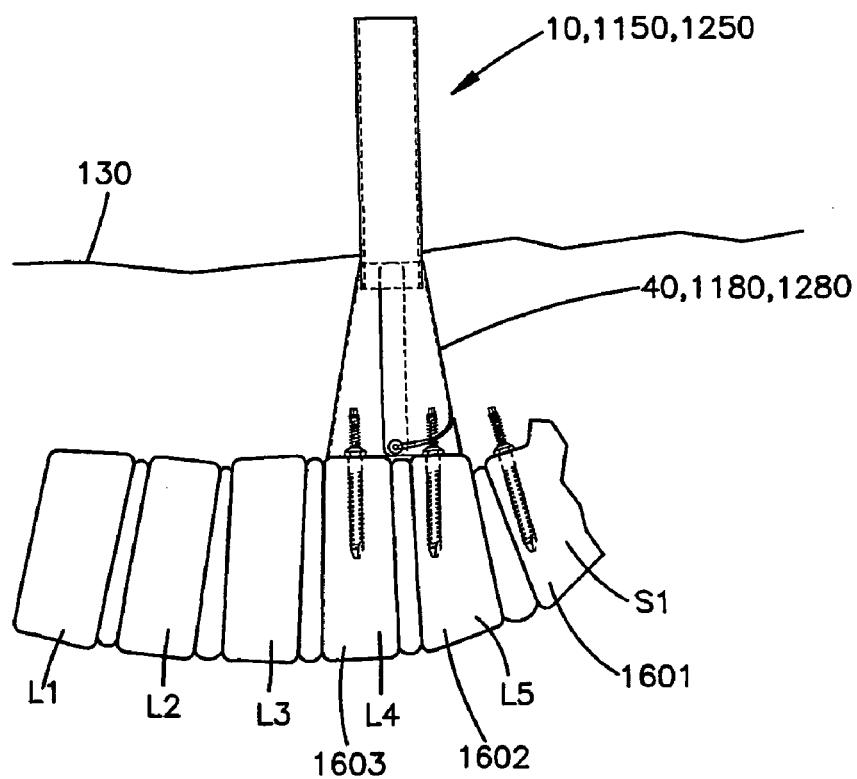
FIG. 35B is a schematic sectional view of another position of the cannula during the surgical procedure of FIG. 35A.
Figure 38:
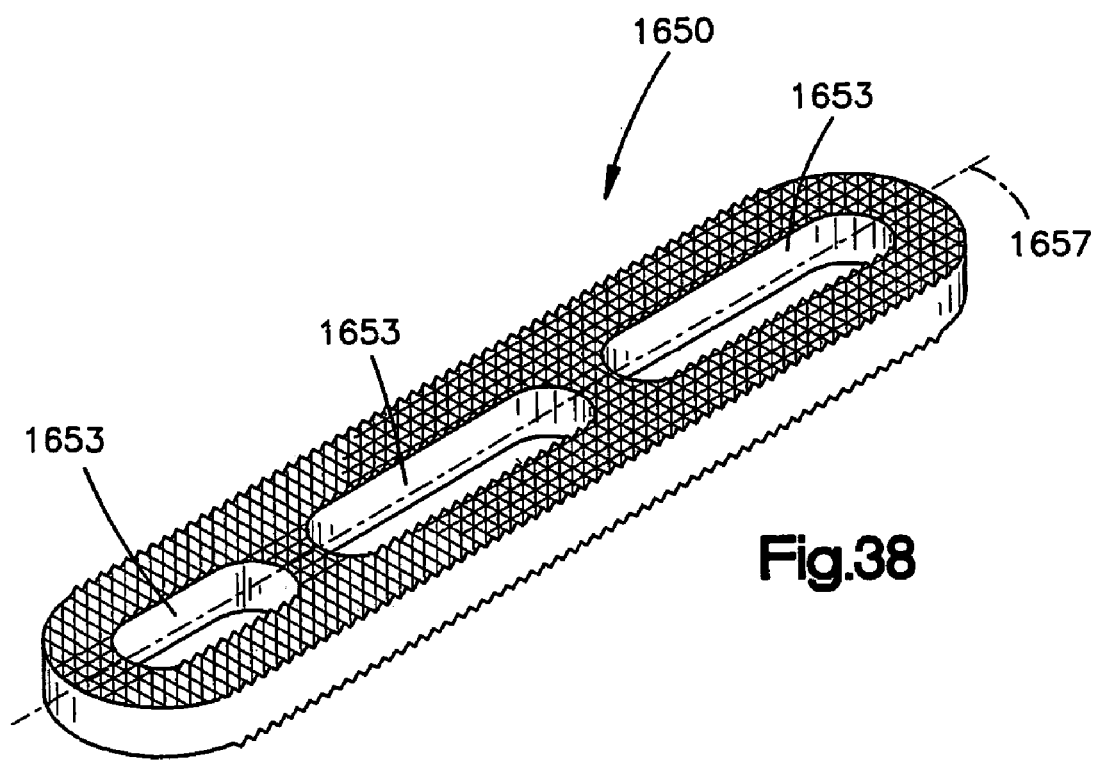
FIG. 38 is a schematic view of part of an alternative fixation element to be attached to vertebrae of a patient, similar to FIG. 29.

The convex and concave engagement surfaces 632, 642, 662, 672 allow angular adjustment of the fixation elements 650, before the locking nuts 670 are fully tightened, when the fasteners 624 are undesirably not threaded into the vertebrae 601, 602 exactly parallel to each other, as shown exaggerated in FIG. 30. These surfaces may typically allow for up to a 12-degree offset angle between the axes of the two fasteners 624.

One of two types of fixation elements 650 may typically be used to secure the two vertebrae 601, 602 or three vertebrae 1601, 1602, 1603 (FIGS. 35a, 35b, 36 and 37) together. The first type may be a spinal plate 651 (FIG. 31) with two slots 653, 655 or a spinal plate 1650 with three slots 1653 extending along the longitudinal axis 657, 1657 of the spinal plate. The second threaded portion 628 of one fastener 624, screwed into the pedicle of one vertebra 601, extends through one slot 653 or 1653 and the second threaded portion 628 of another fastener 624, screwed into the pedicle of another vertebra 602, extends through the other larger slot 655, 1653. The second threaded portion 628 of a third fastener 624, screwed into the pedicle of a third vertebra, may extend through a third slot 1653. Two of the spinal plates 651, one on each side of the vertebrae 601, 602, or 1601, 1602, 1603 are used to secure the two or three vertebrae together, as viewed in FIGS. 29, 35a, 35b, 36, 37. The slots 653, 655 or 1653 allow further transverse adjustment so that the same spinal plate 651 may be used for different size patients.

A second type of fixation element 650 may be two universal side blocks 651a (FIG. 34), each with one slot 653a extending along the longitudinal axis 657a of each side block and a securement opening 655a extending substantially perpendicularly to each slot 653a, as viewed in FIG. 34. The second threaded portion 628 of a fastener 624, screwed into the pedicle of one vertebra 601, extends through one slot 653a and the second threaded portion 628 of another fastener 624, screwed into the pedicle of another vertebrae 602, extends through a slot 653a in an identical side block 651a. The second threaded portion 628 of a third fastener 624, screwed into the pedicle of a third vertebra, may extend through a slot 653a in a third side block 651a. The side blocks 651a further include lower and upper knurled surfaces 652a, 654a similar to the knurled surfaces 652, 654 of the spinal plate 651.

This second type of fixation element 650 further includes a rod 658a extending from the opening 655a in one side block 651a to the opening 655a in the another side block 651a. The rod 658a may extend through the second side block 651a to an opening 655a in a third side block 651a. Set screws 659a secure the rod 658a in each opening 655a when the rod 658a is positioned properly to secure the vertebrae 601, 602 together, as viewed in FIG. 32.

Four of the side blocks 651a, one on each side of each vertebra 601, 602, and two rods 658a are typically used to secure the two vertebrae together. The slots 653a allow further transverse adjustment so that the same side block 651a may be used for different size patients. The rods 658a may also be cut to fit different sized patients. Six of the side blocks 651, one on each side of three vertebrae 1601, 1602, 1603, and two longer rods 658a may be used to secure the vertebrae together (FIGS. 35a, 35b, 36 and 37).

The cannula 10, support apparatus 110, and vertebral fixation assembly 620 (described above) may be used to perform an operation which secures two or three vertebrae together, such as the posterolateral fusion and screw placement, described above. This type of operation traditionally results in much blood loss because of the open access to the spine required for its performance. Utilizing the cannula 10 and support apparatus 110 for placement of the fixation assembly 620 at the surgical site and attachment of the fixation assembly 620 to the vertebrae 601, 602 or 1601, 1602, 1603 in a manner to be described results in a much less invasive procedure and significantly less blood loss.

In accordance with the present invention, a method of fixing two (FIG. 5) or three (FIGS. 35a, 35b, 36 and 37) vertebrae of a patient together at a surgical site includes two main procedures. The first procedure includes the following steps: inserting a first cannula 10, 1150, or 1250 into the body 130 of the patient adjacent one side of the spinal column; inserting a second cannula 10, 1150, or 1250 into the body 130 of the patient adjacent the other side of the spinal column; expanding the second tubular portions 40, 1180, or 1280 of both cannulae (as described above) thereby creating a substantially complete view of both sides of the adjacent vertebrae 601, 602 or 1601, 1602, 1603 utilizing two endoscopes 200 and one or more monitors.

Alternatively, instead of using two cannulae and two endoscopes simultaneously so that both sides of adjacent vertebrae may be worked on by the surgeon at the same time, only one side of the adjacent vertebrae may be worked on and then, subsequently, the other side of the adjacent vertebrae may be worked on. In this case, only one endoscope, one support apparatus 110, and one monitor is required. Typically, two cannulae are used, however, one for each side of the vertebrae.

The second procedure includes the steps of: accessing the vertebrae through the cannulae 10; providing insertion openings, one in each side, or pedicle, of each vertebra utilizing suitable instruments extending through the cannula; inserting fasteners 624 through each cannulae and screwing one fastener into each insertion opening thereby securing each fastener 624 to a vertebra; checking the position of the vertebrae to ensure that the vertebrae have maintained the proper position and, if necessary, repositioning the vertebrae; moving fixation washers 640, 660, locking nuts 670, and fixation elements 650 or 1650 through the cannulae; placing fixation washers 640 and the fixation elements on the fasteners, each fastener extending through one fixation washer and one slot in each fixation element; placing additional fixation washers 660 on the fasteners; and threading the locking nuts onto each fastener thereby fixing the fixation elements to the vertebrae and securing two or three vertebrae together in a natural and permanent position within the body.

Also, bone graft may be moved through the cannula and placed in and around the fixation element 650 or 1650 and fasteners 624 to facilitate fusion of the vertebrae. If necessary, the disk between the vertebrae may be removed through the cannula; the area between the vertebrae cleaned and the vertebrae prepared for receiving a fusion device such as a fusion cage or cages and/or disk replacement material (i.e., autograft, allograft, etc.). This would be done before inserting the fasteners 624 or attaching the fixation elements 650 or 1650. The method may also include inserting, through the cannulae 10, one or more appropriately sized fusion cages and positioning the fusion cage(s) appropriately relative to the vertebrae; and inserting bone graft through the cannulae 10 and positioning the bone graft in and around the fusion cage(s).

The fusion cage may be of any known construction. One typical fusion cage is a hollow rectangular cage that is inserted into grooves that are formed in facing bone surfaces of the vertebrae. Another type of fusion cage is a hollow cylindrical threaded cage that screws into position between the vertebrae. Any suitable fusion cage may be used. Alternatively, instead of a fusion cage, an autograft bone plug (from another portion of the patient's body) or an allograft bone plug (from another body) may be used between vertebrae to facilitate fusion of the vertebrae.

The cannulae 10 (and the tubing 102) are then removed from the body 130 and the incisions are suitably closed. After a time, vertebrae 601, 602 or 1601, 1602, 1603 and bone graft will grow together across the fusion cage(s) and in and around the fixation elements 650 or 1650. The vertebrae will then no longer require the fixation assembly to maintain their position. The fixation elements 650 or 1650 and fasteners 624 may then be removed. The removal procedure may utilize the same type of apparatus as was used in the first and second procedures (i.e., cannula, support apparatus, etc.).

The first and second cannulae 10 may be shifted slightly in the incisions in the body 130 to desired locations within the body at any time during the first and second procedures or the removal procedure. This may be accomplished by changing the position of the support apparatus 110 by manipulating the mechanical arm 301.

In accordance with another feature of the present invention, a method (FIGS. 35a and 35b) of fixing three vertebrae 1601, 1602, 1603 of a patient together includes four main procedures. The first procedure includes the following steps: inserting a first cannula 10, 1150, or 1250 into the body of a patient through a first incision adjacent one side of the spinal column; inserting a second cannula 10, 1150, or 1250 (not shown) into the body of a patient through a second incision adjacent the other side of the spinal column; and expanding the second tubular portions 40, 1180, or 1280 of both the first and second cannulae (as described above) thereby creating a substantially complete view of both sides of two of the three vertebrae utilizing two endoscopes 200 and one or two monitors.

The second procedure includes the following steps: accessing the two vertebrae through the cannulae; providing four insertion openings, one in each side, or pedicle, of each of the two vertebra in view through the cannulae utilizing suitable instruments extending through the cannula 10; inserting fasteners 624 through each cannulae and screwing one fastener into each insertion opening thereby securing each fastener 624 to a vertebra; and checking the position of the vertebrae to ensure that the vertebrae have maintained the proper position and, if necessary, repositioning the vertebrae.

The third procedure includes the step of shifting the first and second cannulae at the incision in order to position the first and second cannulae over each side of the third vertebra that was not viewed previously. This shifting may be accomplished by pivoting the cannulae at the incision or by shifting the cannulae in the body.

The fourth procedure includes the following steps: accessing the third vertebrae through the cannulae; drilling two additional insertion openings, one in each side, or pedicle, of the third vertebra utilizing suitable instruments extending through the cannula, as described above; inserting fasteners 624 through each cannulae and screwing one fastener into each insertion opening thereby securing each fastener 624 to the third vertebra; checking the position of the vertebrae to ensure that the vertebrae have maintained the proper position and, if necessary, repositioning the vertebrae; moving twelve fixation washers 640, 660, six locking nuts 670, and two fixation elements 651*a*, 658*a* or 1650 (FIG. 38) through the cannulae; placing six fixation washers 640 and the fixation elements on the fasteners, each fastener extending through one fixation washer and one slot 653*a* or 1653 in each fixation element; placing the additional fixation washers 660 on the fasteners; and threading the locking nuts onto each fastener thereby fixing the fixation elements to the vertebrae and securing the three vertebrae together in a natural and permanent position within the body. The fixation elements 651*a*, 658*a*, or 1650 would have to be manipulated in the body to be positioned on the fasteners fixed to the three vertebrae 1601, 1602, 1603.

Assuming the discs between the vertebrae are removed, the fusion cages or bone plugs would be moved through the cannulae and positioned between the vertebrae, as determined by the surgeon. Bone graft may also be positioned between the vertebrae. This would be accomplished prior to securing the fixation elements in position on the vertebrae.

In accordance with still another feature of the present invention, a method (FIG. 36) of fixing three vertebrae 1601, 1602, 1603 of a patient together at two surgical sites includes two main procedures. The first procedure includes the following steps: inserting a first cannula 10, 1150, or 1250 into the body 130 of the patient adjacent one side of the spinal column; inserting a second cannula 10, 1150, 1250 into the body 130 of the patient adjacent the other side of the spinal column; expanding the second tubular portions 40, 1040, 1180, or 1280 of both cannulae (as described above) thereby creating a substantially complete view of both sides of the three adjacent vertebrae 1601, 1602, 1603 utilizing two endoscopes 200 and one or more monitors. In this method, the first and second cannulae would, when expanded, be large enough to span three vertebrae.

The second procedure includes the steps of: accessing the vertebrae 1601, 1602, 1603 through the cannulae 10, 1150, or 1250; providing six insertion openings, one in each side, or pedicle, of each vertebra utilizing suitable instruments extending through the cannula; inserting three fasteners 624 through each cannulae and screwing one fastener into each insertion opening thereby securing each fastener 624 to a vertebra; checking the position of the vertebrae to ensure that the vertebrae have maintained the proper position and, if necessary, repositioning the vertebrae; moving twelve fixation washers 640, 660, six locking nuts 670, and two fixation elements 651*a*, 658*a* or 1650 (FIG. 38) through the cannulae; placing six fixation washers 640 and the fixation elements on the fasteners, each fastener extending through one fixation washer and one slot 653*a* or 1653 in each fixation element; placing the additional fixation washers 660 on the fasteners; and threading the locking nuts onto each fastener thereby fixing the fixation elements to the vertebrae and securing the three vertebrae together in a natural and permanent position within the body. Again, assuming the discs between the vertebrae are removed, fusion cages or bone plugs would be moved through the cannulae and positioned between the vertebrae, as determined by the surgeon. Bone graft may also be positioned between the vertebrae. This would be accomplished prior to securing the fixation elements in position on the vertebrae.

In accordance with yet another feature of the present invention, a method (FIG. 37) of fixing three vertebrae 1601, 1602, 1603 of a patient together at two surgical sites includes two main procedures. The first procedure includes the following steps: inserting a first cannula 10, 1150, or 1250 into the body 130 of the patient adjacent one side of the spinal column; inserting a second cannula 10, 1150, 1250 into the body of the patient adjacent the same side of the spinal column; inserting a third cannula 10, 1150, or 1250 into the body of the patient adjacent the other side of the spinal column; inserting a fourth cannula 10, 1150, 1250 into the body of the patient adjacent the other side of the spinal column; expanding the second tubular portions 40, 1040, 1180, or 1280 of the cannulae (as described above) thereby creating a substantially complete view of at least three adjacent vertebrae 1601, 1602, 1603, or 1604 utilizing four endoscopes 200 and one or more monitors.

The second procedure includes the steps of: accessing the vertebrae 1601, 1602, 1603 through the cannulae 10, 1150, or 1250; drilling six insertion openings, one in each side, or pedicle, of each vertebra utilizing suitable instruments extending through the cannula; inserting three fasteners 624 through each cannulae and screwing one fastener into each insertion opening thereby securing each fastener 624 to a vertebra; checking the position of the vertebrae to ensure that the vertebrae have maintained the proper position and, if necessary, repositioning the vertebrae; moving twelve fixation washers 640, 660, six locking nuts 670, and two fixation elements 651*a*, 658*a* or 1650 (FIG. 38) through the cannulae; placing six fixation washers 640 and the fixation elements on the fasteners, each fastener extending through one fixation washer and one slot 653*a* or 1653 in each fixation element; placing the additional fixation washers 660 on the fasteners; and threading the locking nuts onto each fastener thereby fixing the fixation elements to the vertebrae and securing the vertebrae together in a natural and permanent position within the body.

The methods described above may, and most probably do, involve removal of tissue from the surgical site through the cannula 10. Muscle, fat, and bone may be removed through the cannula 10 to provide a proper view of the vertebrae and the location to receive the fixation assembly 620. Different tools may be used in the process of removing tissue. These tools may include a burr and/or tissue cutting blades that are inserted through the cannula 10, 1150, or 1250.

A preferred tissue cutting blade device 710 is shown in FIGS. 39-40. The device 710 has a rotational axis 712 and includes inner and outer cutting tubes 740, 750. Each of the inner and outer tubes 740, 750 has openings 741, 751 into their interiors. Cutting teeth 745, 755 are located on opposite sides of each opening 741, 751.

The inner tube 740 rotates about the axis 712 relative to the outer tube 750 and within the outer tube. The inner tube 740 rotates in opposite directions a predetermined amount equal to one or more revolutions about the axis 712, then rotates in the opposite direction the same predetermined amount. Thus, the inner tube 740 oscillates about the axis 712. As the inner tube 740 oscillates/rotates about the axis 712, the cutting teeth 745, 755 on the inner and outer tubes 740, 750 cut tissue. Alternatively, the inner tube 740 may rotate in one direction (clockwise or counterclockwise) within the outer tube.

During the cutting of tissue, a saline solution or the like may be forced through the annular space 770 between the inner tube 740 and the outer tube 750 to the surgical site. Suction may be applied in the opening 741 of the inner tube 740 to remove the cut tissue and the saline solution from the surgical site.

A tubular sheath 760 receives the inner and outer cutting tubes 740, 750. The sheath 760 extends along the length of the cutting tubes 740, 750 and adjacent a distal end of the cutting tubes where the cutting teeth 745, 755 are located. The sheath 760 is a stainless steel tube that is electrically insulated along its length from the patient's body and from the outer tube 750. An electrical insulator 763, such as a suitable polymer coating, is provided over the outside and inside surfaces of the sheath 760. However, a selected area 762 of the outside surface of the sheath 760 adjacent the distal end of the cutting tubes 740, 750 is not coated with the insulator 763. A portion 765 of the distal end of the sheath 760 is cut away so that the cutting teeth 745, 755 on the cutting tubes 740, 750 are not blocked by the sheath 760 from cutting tissue.

An electric current from a current source 766 may be applied to the sheath 760. The electric current flows through the sheath 760 and to the selected uncoated area 762 of the sheath. The current then flows through tissue and blood into the distal end of the outer cutting tube 750 and back to the current source through the outer cutting tube to form a completed circuit.

The current flow through the electrically energized sheath 760 and outer cutting tube 750 serves to electrocoagulate blood in the cutting area at the surgical site. Electrocoagulation of blood is known and any other suitable electrocoagulation device may alternatively be used.

From the above description, one skilled in the art should realize that viewing of the surgical site may be performed without using an endoscope. A microscope or glasses that magnify the site may be used. In fact, any suitable viewing device may be used. Also, the procedure discussed above mentions providing openings in the vertebrae. Any suitable method (i.e., drilling, using an awl or other instrument to form an opening to receive a fastener, etc.) may be used.

Also, from the above description of the invention, those skilled in the art will perceive improvements, changes and modifications. Such improvements, changes and modifications within the skill of the art are intended to be covered by the appended claims.

Having described the invention, the following is claimed:

1. A method of fixing vertebrae of a patient together at a surgical site comprising the steps of:
   inserting a first access device into the body of the patient;
   moving a first fastener through the access device and securing the first fastener to a first vertebrae;
   moving a second fastener through the access device and securing the second fastener to a second vertebrae;
   moving a first fixation element through the access device; and
   fixing the first fixation element to the first and second fasteners; wherein the first and second fasteners and the first fixation element are all moved through the same access device with the access device in a first position.

2. A method as defined in claim 1 further including the steps of:
   inserting a second access device into the body of the patient;
   moving a third fastener through the second access device and securing the third fastener to the first vertebrae;
   moving a fourth fastener through the second access device and securing the fourth fastener to the second vertebrae;
   moving a second fixation element through the second access device; and fixing the second fixation element to the third and fourth fasteners.

3. A method as defined in claim 2 further including the steps of expanding the first access device at its end adjacent the first and second vertebrae and expanding the second access device at its end adjacent the first and second vertebrae.

4. A method as defined in claim 3 further including the step of shifting the first and second access devices in the body to position the first and second access devices to desired locations in the body.

5. A method as defined in claim 1 further including the step of expanding the first access device at its end adjacent the first and second vertebrae.

6. A method as defined in claim 1 further including the step of positioning an endoscope in the first access device to provide a view of the activity at the surgical site.

7. A method as defined in claim 6 further including the steps of:
   removing a disk from between the first and second vertebrae; cleaning the area between the first and second vertebrae; and
   positioning at least one fusion device between the first and second vertebrae by moving a fusion device through the access device.

8. A method as defined in claim 6 further including the step of positioning an endoscope in the second access device to provide a view of the activity at the surgical site.

9. A method as defined in claim 8 wherein the first fixation element is a plate and said step of fixing the first fixation element to the first and second fasteners includes a step of positioning the plate with the first and second fasteners extending through openings in the plate and moving first and second nuts through the access device and threading the nuts onto the first and second fasteners.

10. A method as defined in claim 8 wherein the first fixation element is a rod and said step of fixing the first fixation element to the first and second fasteners includes positioning the rod to extend adjacent the first and second fasteners and between the first and second vertebrae.

11. A method as defined in claim 8 further including the steps of:
   removing a disk from between the first and second vertebrae; cleaning the area between the first and second vertebrae; and
   positioning at least one fusion device between the first and second vertebrae by moving a fusion device through the access device.

12. A method as defined in claim 1 further comprising the step of cutting away tissue at the surgical site.

13. A method as defined in claim 12 further comprising the step of utilizing a blood coagulation sheath for coagulating blood.

14. A method as defined in claim 1 wherein said step of securing the first fastener to the first vertebra includes the step of screwing the first fastener into the first vertebra and said step of securing the second fastener to the second vertebra includes the step of screwing the second fastener into the second vertebra.

15. A method as defined in claim 1 wherein the first fixation element is a plate and said step of fixing the first fixation element to the first and second fasteners includes a step of positioning the plate with the first and second fasteners extending through openings in the plate and moving first and second nuts through the access device and threading the nuts onto the first and second fasteners.

16. A method as defined in claim 1 wherein the first fixation element is a rod and the step of fixing the first fixation element to the first and second fasteners includes positioning the rod to extend adjacent the first and second fasteners and between the first and second vertebrae.

17. A method as defined in claim 1 further including the steps of:
removing a disk from between the first and second vertebrae; cleaning the area between the first and second vertebrae; and
positioning at least one fusion device between the first and second vertebrae by moving a fusion device through the access device.

18. A method of fixing vertebrae of a patient together at a surgical site as defined in claim 1 further including the steps of:
moving a third fastener through the access device and securing the third fastener to a third vertebrae, and
fixing the first fixation element to the third fastener as well as to said first and second fasteners.

19. A method as defined in claim 18 further including the step of expanding the first access device in the patient's body at its end adjacent the first, second, and third vertebrae.

20. A method as defined in claim 19 wherein, prior to moving a third fastener through the access device, the access device is shifted to a second position in the patient's body.

21. A method as defined in claim 19 wherein the expanded first access device is large enough to not require shifting of the first access device in the patient's body.

22. A method as defined in claim 1 further including the steps of:
inserting a second, third, and fourth access device into the body of the patient;
expanding the second, third, and fourth access devices in the patient's body adjacent the first and second vertebrae; and
viewing the first and second vertebrae and a third vertebrae through the first, second, third, and fourth access devices.

23. A method of performing a surgical procedure on a body comprising the steps of:
providing a access device having a tubular structure with first and second tubular portions defining first and second paths for receiving surgical instruments, the second path being a continuation of the first path, the second tubular portion having a first edge that overlaps a second edge;
inserting the access device through an incision in the body, said inserting step including inserting the second tubular portion inside the body and inserting the first tubular portion into the incision so that the first tubular portion extends from an exterior of the body to inside the body;
expanding the second tubular portion of the access device from a cylindrical configuration into a conical configuration to increase the cross-sectional area of the second path in the second tubular portion while the second tubular portion is inside the body, wherein said expanding includes moving the first edge of the second tubular portion relative to the second edge of the second tubular portion wherein the first edge overlaps the second edge in the cylindrical and conical configurations; and
maintaining the cross-sectional area of the first path in the first tubular portion while expanding the second tubular portion of the access device.

24. A method of performing a surgical procedure as set forth in claim 23 wherein said step of expanding the second tubular portion of the access device includes applying a radially outwardly directed force to the second tubular portion to expand the second tubular portion.

25. A method of performing a surgical procedure as set forth in claim 23 wherein said step of moving the first edge of the second tubular portion relative to the second edge of the second tubular portion includes guiding movement of the first edge relative to the second edge.

26. A method of performing a surgical procedure as set forth in claim 25 wherein said step of guiding movement of the first edge relative to the second edge includes moving a guide member connected with one of the first and second edges along an arcuate slot extending through the second tubular portion adjacent to the other one of the first and second edges.

27. A method of performing a surgical procedure as set forth in claim 26 wherein said step of moving the guide member along the slot includes moving the guide member along an arcuate slot extending through the second tubular portion.

28. A method of performing a surgical procedure as set forth in claim 23 wherein said step of moving the first edge relative to the second edge includes pivoting at least one of the first and second edges relative to the first tubular portion.

29. A method of performing a surgical procedure as set forth in claim 23 wherein said step of inserting the access device through the incision in the body includes maintaining the second tubular portion in a contracted condition while inserting the access device through the incision.

30. A method of performing a surgical procedure as set forth in claim 29 wherein said step of maintaining the second tubular portion in the contracted condition while inserting the access device through the incision includes covering the second tubular portion of the access device with a removable member.

31. A method of performing a surgical procedure as set forth in claim 30 wherein said step of expanding the second tubular portion of the access device includes removing the removable member from the second tubular portion of the access device after the second tubular portion is inserted inside the body.

32. A method of performing a surgical procedure as set forth in claim 31 wherein said step of removing the removable member includes pulling a string wrapped around the removable member to tear the removable member.

33. A method of performing a surgical procedure as set forth in claim 23 wherein said step of expanding the second tubular portion of the access device includes inserting a tool into the second path in the access device.

34. A method of performing a surgical procedure as set forth in claim 33 wherein said step of expanding the second tubular portion of the access device includes moving first and second portions of the tool apart after the tool is inserted into the second path in the access device.

35. A method of performing a surgical procedure as set forth in claim 34 wherein said step of moving the first and second portions of the tool apart includes moving first and second frustoconical halves of the tool apart.

36. A method of performing a surgical procedure as set forth in claim 34 wherein said step of expanding the second tubular portion of the access device includes rotating the tool relative to the access device.

37. A method of performing a surgical procedure as set forth in claim 23 further including providing the first tubular portion of the access device with a first thickness measured in a direction perpendicular to inner and outer surfaces of the first tubular portion, providing the second tubular portion of the access device with a second thickness measured in a direction perpendicular to inner and outer surfaces of the second tubular portion with the first thickness being different from the second thickness.

38. A method of performing a surgical procedure as set forth in claim 37 wherein said step of providing the second tubular portion with a second thickness includes providing the second tubular portion with a second thickness that is less than the first thickness.

39. A method of performing a surgical procedure as set forth in claim 38 wherein said step of providing the second tubular portion with a second thickness that is less than the first thickness includes providing the second tubular portion with a thickness in the range of 0.003 inches to 0.005 inches.

40. A method of performing a surgical procedure as set forth in claim 39 wherein said step of providing the second tubular portion with a second thickness that is less than the first thickness includes providing the first tubular portion with a thickness in the range of 0.02 inches to 0.04 inches.

41. A method of performing a surgical procedure as set forth in claim 23 further including providing the first path in the proximal end with a diameter in the range of 10mm to 20mm.

42. A method of performing a surgical procedure as set forth in claim 41 further including providing the second path in the second tubular portion with a diameter in the range of 40% to 80% greater than the diameter of the first path in the first tubular portion when the second tubular portion is in an expanded condition.

43. A method of treating the spine of a patient, the method comprising the steps of:
  making an incision in the patient's skin;
  introducing a retractor into the incision for placement at a surgical site, the retractor comprising:
    a proximal end and a distal end, the proximal end having an access opening positioned outside the patient and the distal end sized for insertion into the incision in the patient;
    the retractor being configured for an unexpanded configuration during insertion into the incision and an expanded configuration when located at a surgical site in the patient;
    the retractor when in the expanded configuration configured to provide maximum tissue retraction at the distal end, and
    the retractor having sufficient rigidity to retract tissue;
  engaging the retractor with an expander;
  moving the retractor from the unexpanded configuration to the expanded configuration with the expander;
  passing an instrument through the retractor to remove tissue from a disk space located between adjacent vertebral bodies;
  inserting one or more fusion devices through the retractor and into the disk space;
  inserting fasteners through the retractor and coupling the fasteners to the adjacent vertebral bodies;
  inserting a fixation element through the retractor and connecting the fixation element between the fasteners; and
  removing the retractor from the incision in the patient;
  wherein the steps of inserting one or more fusion devices, fasteners, and a fixation element through the retractor are all performed through the same retractor, without re-positioning the retractor.

\* \* \* \* \*